(12) United States Patent
Sheetrit et al.

(10) Patent No.: US 10,039,865 B2
(45) Date of Patent: Aug. 7, 2018

(54) IMPLANTABLE DEVICE COMPRISING A SUBSTRATE PRE-COATED WITH STABILIZED FIBRIN

(75) Inventors: Eyal Sheetrit, Shoam (IL); Israel Nur, Nes-Ziona (IL); Liliana Bar, Rehovot (IL); Lior Weissman, Nes-Ziona (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 412 days.

(21) Appl. No.: 12/563,667

(22) Filed: Sep. 21, 2009

(65) Prior Publication Data

US 2010/0076464 A1 Mar. 25, 2010

Related U.S. Application Data

(60) Provisional application No. 61/099,174, filed on Sep. 22, 2008.

(30) Foreign Application Priority Data

Feb. 3, 2009 (EP) .................................... 09151987

(51) Int. Cl.
*A61L 31/14* (2006.01)
*A61L 31/10* (2006.01)

(52) U.S. Cl.
CPC .............. *A61L 31/143* (2013.01); *A61L 31/10* (2013.01)

(58) Field of Classification Search
USPC ......... 514/12; 527/200; 427/2.1, 372.2, 569, 427/2.3, 2.25, 2.28, 355, 235, 232, 2.31, 427/338, 2.24, 377; 600/37
See application file for complete search history.

(56) References Cited

U.S. PATENT DOCUMENTS

| | | | |
|---|---|---|---|
| 5,272,074 A | 12/1993 | Rubens | |
| 5,660,873 A * | 8/1997 | Nikolaychik et al. | 427/2.24 |
| 5,792,835 A | 8/1998 | Tse et al. | |
| 5,843,436 A | 12/1998 | Loike et al. | |
| 6,121,232 A | 9/2000 | Nur et al. | |
| 6,153,252 A * | 11/2000 | Hossainy et al. | 427/2.3 |
| 7,125,569 B2 | 10/2006 | Nur et al. | |
| 2001/0008930 A1* | 7/2001 | Tayot et al. | 527/200 |
| 2005/0010239 A1 | 1/2005 | Chefitz | |

(Continued)

FOREIGN PATENT DOCUMENTS

| | | |
|---|---|---|
| EP | 0534178 | 4/2001 |
| EP | 1390485 | 10/2006 |

(Continued)

OTHER PUBLICATIONS

Brown, G.L. et al 'Comparison of Prosthetic Materials for Abdominal Wall Reconstruction in the Presence of Contamination and Infection' Ann Surg. (1985) vol. 201, No. 6 pp. 705-709.

(Continued)

*Primary Examiner* — Dah-Wei D Yuan
*Assistant Examiner* — Andrew Bowman
(74) *Attorney, Agent, or Firm* — David R. Crichton

(57) ABSTRACT

The invention relates to a prosthetic for repairing an opening or a defect in a soft tissue, to its preparation and use. The prosthetic of the invention comprises a substrate viscerally-coated with stabilized and non-completely dry fibrin. The prosthetic displays reduced postoperative complications following its implantation.

9 Claims, 5 Drawing Sheets

(56) References Cited

U.S. PATENT DOCUMENTS

| | | | |
|---|---|---|---|
| 2005/0100654 A1* | 5/2005 | Su et al. | 427/2.1 |
| 2006/0015004 A1* | 1/2006 | Sitzmann | 600/37 |
| 2009/0075891 A1* | 3/2009 | MacPhee et al. | 514/12 |

FOREIGN PATENT DOCUMENTS

| | | |
|---|---|---|
| WO | WO 93/05822 | 4/1993 |
| WO | WO 98/33533 | 8/1998 |
| WO | WO 02/095019 | 11/2002 |
| WO | WO 09/019685 | 2/2009 |

OTHER PUBLICATIONS

Ellis, H. 'The Causes and Prevention of Intestinal Adhesions' Br. J. Surg. (1982) vol. 69 pp. 241-243.

Ellis, H. 'The Clinical Significance of Adhesions: Focus on Intestinal Obstruction' Eur J Surg (1997), Suppl. 577. pp. 5-9.

Kayaoglu, H.A. et al 'Comparison of Adhesive Properties of Five Different Prosthetic Materials Used in Hernioplasty' J. Invest. Surg. (2005) vol. 18 pp. 89-95.

Martin-Cartes, J.A. et al 'Role of Fibrin Glue in the Prevention of Peritoneal Adhesions in Ventral Hernia Repair' Surgery Today (2008) vol. 38, No. 2 pp. 135-140.

Mehall, J.R. et al 'Fibrin Sheath Enhances Central Venous Catheter Infection' Crit Care Med (2002) vol. 30, No. 4 pp. 908-912.

Skarja, G.A. et al 'Protein and Platelet Interactions with Thermally Denatured Fibrinogen and Cross-Linked Fibrin Coated Surfaces' Biomaterials. (1998) vol. 19, No. 23 pp. 2129-2138.

Toosie K., et al. "Fibrin Glue Reduces Intra-Abdominal Adhesions to Synthetic Mesh in a Rat Ventral Hernia Model" Am Surg. (2000) vol. 66, No. 1 pp. 41-45.

Troller, J.A. et al 'Measurement of Water Activity' *Compendium of Methods for the Microbiological Examination of Foods*. American Public Health Association. Washington DC. 2nd Edition. (1984) pp. 124-134.

International Preliminary Report re: PCT/IL2009/000909 dated Mar. 22, 2011.

International Search Report re: PCT/IL2009/000909 dated Sep. 28, 2010.

Wang, M-C et al., 'Preparation of fibrin glue: the effects of calcium chloride and sodium chloride' Materials Science and Engineering (1995) C 3 pp. 131-135.

Extended European Search Report re: 09151987.6 dated Jul. 6, 2009.

\* cited by examiner

IMPLANTABLE DEVICE COMPRISING A SUBSTRATE PRE-COATED WITH STABILIZED FIBRIN

This application is a Non-Provisional claiming priority of EP Application No. 09151987.6 filed on Feb. 3, 2009, which claims priority from U.S. Provisional Application No. 61/099,174, which was filed on Sep. 22, 2008, the contents of all of which are hereby incorporated by reference.

FIELD OF THE INVENTION

The invention relates to an implantable device comprising a substrate coated with stabilized and non completely dried fibrin and uses thereof.

BACKGROUND OF THE INVENTION

A hernia occurs when the content of a body cavity bulge out of the area where it is normally contained. There are many different types of hernias which are classified according to their anatomical location. The most common type of hernia is in the abdomen region, in which a weakness in the abdominal wall evolves into a localized hole, or a "defect", through which abdominal organs may protrude.

Hernias usually need to be surgically repaired to prevent organ dysfunction and further complications. The repair is typically performed by reinforcing the muscle with surgical mesh prosthesis. Surgical complications may include surgical site infection, postoperative adhesions, bacterial contamination, hernia recurrence or chronic pain.

In recent years, fibrin glues are used increasingly in various clinical and surgical settings to decrease postoperative adhesion formation. In practice, the fibrin glue components are sprayed onto the operated site.

Fibrin glues are also known as fibrin sealants or fibrin adhesives. They are typically obtained by mixing a fibrinogen component and a thrombin component. Mixing both components mimics the physiological reaction of fibrin formation as it occurs in the blood circulation during the last step of the coagulation cascade, when thrombin converts the fibrinogen to fibrin by an enzymatic action. However, there is one major difference, the concentration of both fibrinogen and thrombin in the fibrin glue components are at least 20 times higher than their concentration in the plasma. For example, fibrinogen concentration in the plasma is about 2-3 mg/ml whereas fibrinogen concentration in the fibrin flue formulation is about 70-100 mg/ml. These attributes contribute to the physical nature and to the longevity of the formed clot.

The fibrinogen component may also contain other plasma proteins such as factor VIII, factor XIII, fibronectin, vitronectin and von willebrand factor. Some manufacturers add anti-proteolytic agents to the fibrin glue formulation (as described in WO-A-93/05822) or specifically remove the plasminogen in order to stop or delay the fibrinolysis (as described in U.S. Pat. No. 5,792,835 and U.S. Pat. No. 7,125,569). When the components are mixed the fibrin clot is formed and adheres to the application site. The physical properties of the fibrin sealant enables it to act as a fluid-tight sealing agent and stop bleeding and/or to seal tissues and surgical materials, such as graft, in a desired configuration. The tight fibrin structure, formed by a high concentration of thrombin, also forms a physical barrier that prevents infiltration of inflammatory cells, bacteria and omentum into the injured tissue consequently resulting in reduced local inflammatory reaction, reduced adhesion formation and reduced bacterial proliferation.

Martin-Cartes et al. (Sorg. Today 2008 38:135-140) discloses that a reduction in both the quantity and consistency of adhesions was observed in implanted prostheses covered with fibrin glue used in ventral hernia repair. In these studies the prostheses were placed at the site of surgery and covered with fibrin glue on the visceral side during the course of the surgical procedure. The draw back of spraying the fibrin glue onto a surgical mesh placed within the surgery area is that the process is time-consuming and is technically hard to perform while working through small incisions and under artificial lightening such as in laparoscopic procedure due to an inaccurate assessment of the thickness and the position of the fibrin glue on the surface of the mesh. In addition, the fibrin glue components can exit from the desired location either due to rinsing or surgeon error resulting in a relatively low volume of fibrin glue applied to the injured surface and in a non uniform layer of the applied material.

Fibrin glue pre-coated devices for vascular grafts have been disclosed. In these devices the fibrin coating is dry, present on the intraluminal side of the vascular graft and allows grow of endothelial cells inside the graft.

U.S. Pat. No. 5,272,074 provides methods for coating surfaces of polymeric materials with fibrinogen and fibrin through a process of heat denaturation. Described is that the adherence of fibrinogen to polymeric surfaces can be greatly enhanced by thermal denaturation of the D-domain of fibrinogen. It is disclosed that polymerized fibrin coated surfaces may be stabilized by treatment with thrombin, factor XIII and additional fibrinogen. It is indicated that the methods of coating are suitable for coating surfaces of prosthetic devices that are exposed to blood flow such as vascular grafts, artificial heart valves and cardiac assist device.

U.S. Pat. No. 5,660,873 is directed to a method for coating a surface of a substrate with fibrin. It is disclosed that the fibrin coated substrate is dried to yield a dried fibrin-coated substrate suitable for substrates that are exposed to blood flow such as intraluminal stents thereby creating devices with a low risk of inducing clot formation. The above patents are silent on a hernia mesh device.

US-A-2005/0010239 discloses a mesh device for surgical repair of hernia which contains a tissue adhesive. It is disclosed that the tissue adhesive within the mesh is activated after the mesh-device has been placed in the patient's body for securing the mesh in place without the need of sutures, staples or other securing apparatus.

WO 2009/019685 discloses a mesh comprising a first layer made of fibrin and allows cellular adhesion and a substantially non-porous second layer characterized by non-adhesion. In use the first layer is adhered to the tissue of the abdominal wall and enables wall tissues infiltration into the layer.

There is clearly an unmet need for a surgical prosthetic implant with reduced postoperative complications.

SUMMARY OF THE INVENTION

The invention relates to a prosthetic or implantable device comprising a substrate having a visceral surface coated with fibrin wherein such fibrin is stabilized on the substrate. Advantageously, the fibrin is stabilized on the substrate without employing intensive drying (e.g. drying without undergoing lyophilization (freeze drying) or spray drying procedures). In one method of the invention the fibrin is stabilized on the substrate by inclusion of a high concentration of solute such as salt in the fibrin coating composition.

Fibrin glue coated devices have been described, however, the device of the invention is able to strongly adhere to the damaged tissue and to diminish surgery related complications such as adhesions, microbial and/or bacterial colonization, damage recurrence and/or infection. Advantageously, the device according to the invention can be stored for extended periods of time before use. The device of the invention is sufficiently flexible to be easily delivered during laparoscopic procedure.

In one aspect, the invention provides a method for producing an improved implantable device for repairing an opening or a defect in a soft tissue, the method comprising the steps of: providing a substrate having a visceral surface and a non-visceral surface; forming a fibrin coating on at least a portion of the visceral surface by applying to that portion a defined volume of a solution comprising fibrinogen and a solution comprising a proteolytic enzyme which is capable of forming fibrin when it reacts with fibrinogen; and drying the coating, thereby obtaining an improved implantable device comprising a stabilized fibrin coating, the device is capable of displaying reduced postoperative complications.

In one embodiment of the invention, the postoperative complications are selected from the group consisting of adhesions, bacterial contamination, infections, opening or defect recurrence and a combination thereof.

In another embodiment of the present invention, the surface of the substrate is activated prior to forming the fibrin coating. The surface activation can be carried out by plasma treatment.

In another further embodiment of the present invention, the proteolytic enzyme is thrombin.

Yet in another embodiment of the invention, the fibrin forming step is carried out by first applying to the visceral surface a solution comprising fibrinogen and second applying to the visceral surface a solution comprising a proteolytic enzyme which is capable of forming fibrin when it reacts with fibrinogen.

Yet in another further embodiment of the invention, the substrate is porous. The substrate can be a mesh.

Still in another embodiment of the invention, the opening or defect is a hernia.

In one embodiment of the invention, device is implanted using laparoscopic procedure. The device can be used in contaminated or a potentially contaminated area.

Still in another further embodiment of the invention, a solute capable of binding free water and having a molecular weight of about 1,000 Dalton or less is added prior to the drying step. The solute can be added prior to fibrin formation.

Yet in another embodiment of the invention, the solute is selected from the group consisting of amino acids such as tranexamic acid, arginine hydrochloride, lysine hydrochloride and salts thereof; salts such as calcium chloride, potassium chloride, sodium chloride, tri-sodium citrate; saccharides such as sucrose and maltose; polyols such as polyglycerol; sugar alcohols such as mannitol and xylitol and a combination thereof. In one embodiment of the invention, the solute is a salt.

The salt content in the fibrin coating following drying can be in the range of about 5%-68%. In one embodiment of the present invention, the salt content in the fibrin coating following drying is in the range of about 20%-68%, in the range of about 20%-32%, or in the range of about 51%-68%.

The solutions can be applied by using a liquid dispenser.

In one embodiment of the present invention, the drying is carried out by non intensive drying. In another embodiment of the invention, the coating is air dried. The temperature during the drying step can be less than 37° C.

In another further embodiment of the invention, the fibrin coating has a water activity of equal to or less than 0.6 following the drying step.

Yet in another further embodiment of the invention, the fibrin coating comprises residual water following the drying step.

Still in another embodiment of the invention, the water content in the coating is in the range of about 3%-20%, equal to or less than 15%, equal to or less than 10%, or equal to or more than 3%.

Still in another further embodiment of the invention, the coating comprises a water content in the range of about 3%-20% and a salt content in the range of about 20%-68% following the drying step.

In another aspect, the invention relates to an implantable device for repairing an opening or a defect in a soft tissue, the device comprises a substrate having a visceral surface and a non-visceral surface, wherein said visceral surface comprises a stabilized fibrin coating.

In one embodiment of the invention, the opening or defect is a hernia.

In another embodiment of the invention, the coating comprises a solute capable of binding free water having a molecular weight of about 1,000 Dalton or less.

In another further embodiment of the invention, the solute is selected from the group consisting of amino acids such as tranexamic acid, arginine hydrochloride, lysine hydrochloride and salts thereof; salts such as calcium chloride, potassium chloride, sodium chloride, tri-sodium citrate; saccharides such as sucrose and maltose; polyols such as polyglycerol; sugar alcohols such as mannitol and xylitol and combination thereof. In one embodiment of the invention, the solute is a salt. In another embodiment of the invention, the salt content in the fibrin coating is in the range of about 5%-68%, in the range of about 20%-68%, in the range of about 20%-32%, or in the range of about 51%-68%.

In one embodiment of the invention, the coating has a water activity of equal to or less than 0.6. In another embodiment of the invention, the majority of said visceral surface is coated.

In another further embodiment of the invention, the coating is not completely dry. Still in another embodiment of the invention, the coating comprises water in the range of about 3%-20%, equal to or less than 15%, equal to or less than 10%, equal to or more than 3%.

Yet in another embodiment of the invention, the coating comprises a water content in the range of about 3%-20% and salt content in the range of about 20%-68%.

Yet in another further embodiment of the invention, the substrate is porous. In one embodiment of the invention, the substrate is a mesh.

The device according to the invention can be implanted in a laparoscopic procedure. The device according to the invention can be used in contaminated or a potentially contaminated area.

Another object of the invention is to provide a surgical implantable device for repairing an opening or a defect in a soft tissue, the device is capable of reducing surgically related complications selected from the group consisting of postoperative adhesions, bacterial contamination, opening or defect recurrence, infections and combination thereof, the device comprises a substrate having a visceral surface and a non-visceral surface, wherein the visceral surface is at least partially coated with a coating comprising stabilized fibrin.

In one embodiment of the invention, the opening or defect is a hernia. In another embodiment of the invention, the substrate is porous. In another further embodiment of the invention, the substrate is a mesh.

Still in another embodiment of the invention, the majority of the visceral surface is coated. The device of the invention can be implanted in a laparoscopic procedure. The device of the invention can be used in contaminated or a potentially contaminated area.

In one embodiment of the invention, the coating comprises a solute capable of binding free water having a molecular weight of about 1,000 Dalton or less. In another embodiment of the invention, the solute is selected from the group consisting of amino acids such as tranexamic acid, arginine hydrochloride, lysine hydrochloride and salts thereof; salts such as calcium chloride, potassium chloride, sodium chloride, tri-sodium citrate; saccharides such as sucrose and maltose; polyols such as polyglycerol; sugar alcohols such as mannitol and xylitol and combination thereof.

In one embodiment of the invention, the solute is a salt. In another embodiment of the invention, the salt content in the fibrin coating is in the range of about 5%-68%, in the range of about 20%-68%, in the range of about 20%-32%, or in the range of about 51%-68%.

In another embodiment of the invention, the coating is not completely dry. In another further embodiment of the invention, the coating comprises water in the range of about 3%-20%.

Still another aspect of the invention is to provide a kit comprising: a first container comprising an implantable device according to the invention, a second container comprising a re-hydration solution, and instructions for use.

An object of the present invention is also to provide a package containing a sterilized implantable device according to the invention.

Still another aspect of the invention is to provide a method for repairing an opening or a defect in a soft tissue in a patient in need, the method comprising the steps of: providing an implantable device according to the invention; and applying the device adjacent to the opening and/or defect.

In one embodiment of the invention, the repair is carried out by a laparoscopic procedure. In another embodiment of the invention, the tissue is contaminated or a potentially contaminated area.

In another further embodiment of the invention, the opening or defect is a hernia. Still in another embodiment of the invention, the device is re-hydrated in an aqueous solution prior to its application.

The step of applying can be carried out such that the visceral surface is facing the internal organs of the patient and the non visceral surface is facing the opening or the defect.

In one embodiment of the invention, the device displays reduced surgically related complications selected from the group consisting of adhesions, bacterial contamination, opening or defect recurrence, infections and a combination thereof.

The implantable device according to the invention, the kit according to the invention, or the package according to the invention can be used for repairing an opening or a defect in a soft tissue.

DETAILED DESCRIPTION OF THE INVENTION

Figure 1A:
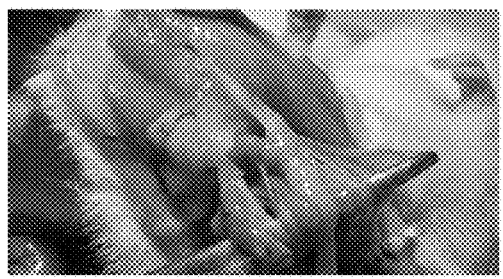
FIGS. 1-2 show the adhesion level in the surgery area 14 and 30 days following surgery, respectively, in control groups (A), 0.3 ml applied fibrin sealant (B), and 0.6 ml applied fibrin sealant (C).

The invention relates to a prosthetic or implantable device for repairing an opening or a defect in a soft tissue. The device comprises a substrate pre-coated with stabilized fibrin. A coating of stabilized fibrin is for example, a coating of dried fibrin which does not flake from the device and/or a coating of fibrin which does not deteriorate for at least 2-3 weeks at non freezing temperature storage conditions e.g. at a temperature of 2-8° C. and up to room temperature such as less than 37° C. and/or under non sterile conditions. In one embodiment of the invention, the coating is stable for 1 year when stored at room temperature. The term "soft tissue" refers to structures of the body that connect, support envelope and/or or surround other structures and organs. Examples of soft tissue include, but are not limited to, fascia, muscles, muscle wall, fat tissue, and blood vessels.

The term "a coating which does not flake" refers to a coating which is substantially continuous, a coating which does not break and/or a coating which does not crumble into individual pieces. In one embodiment of the invention, the coating does not break and/or crumbles into individual pieces even in a rolled or folded form when delivered through a trocar during laparoscopic procedure.

In one embodiment of the invention, the stability of the coating can be assessed by a visual inspection of the coating structure taking into consideration the continuity of the coating and/or the flakiness of the coating from the surface of the device. The visual inspection can be carried out before or after re-hydration of the implantable device in water and/or salt solution such as saline.

It has been found according to the present invention that an implantable surgical device comprising a substrate coated with stabilized fibrin can be obtained using a non completely dry fibrin which has a high concentration of a solute capable of binding free water and having a molecular weight of about 1,000 Dalton or less. Thus, in one embodiment of the invention, the coating comprises a solute. In another embodiment of the invention, the solute used is a salt As used herein the term "solute" refers to a water-soluble agent. Non limiting examples of solutes are amino acids such as tranexamic acid, arginine hydrochloride, lysine hydrochloride and salts thereof. In one embodiment of the invention, tranexamic acid salt is used. In another embodiment of the invention, organic or inorganic salts can be used. Examples of salts include, but are not limited to, calcium chloride, potassium chloride, sodium chloride, tri-sodium citrate and mixtures thereof.

Other solutes which bind free water can also be used including saccharides such as sucrose and maltose; polyols such as polyglycerol; sugar alcohols such as mannitol and xylitol. It is also possible herein that the coating comprises a combination of the above specified solutes.

It is desirable to have in the dried fibrin coating some residual water to allow reduction of flakiness and/or to increase the flexibility of the implantable device. It is also desirable that the dried fibrin coating have a low water activity to minimize bacterial growth while in storage.

Advantageously, the implantable device comprises a stable coating of dried fibrin which does not deteriorate and at the same time comprises a sufficient water content which facilitates maintaining the continuity and the flexibility of the coating. In one embodiment of the invention, the device is also sufficiently flexible to be delivered in a laparoscopic procedure and/or to be able to conform to the body surface.

The water activity ($a_w$) of the stabilized fibrin coating can be equal to or less than 0.6 such as 0.5 and 0.4. Within the context of this invention the term "water activity" refers to the water in the coating that is free and available for microbial and/or bacterial growth. The growth of specific microorganisms is limited below a certain specific water activity. These limits are well defined in scientific literature (JA. Troller, D T. Bernard and V W Scott. Measurement of water activity. In: Compendium of Methods for the Microbiological Examination of Foods. American public health association Washington D.C., 1984 pp. 124-134). For example, below 0.6 $a_w$, water is so tightly bound that it is unavailable to even the most xerophytic fungi.

Water activity can greatly affect microbial action, safety profile, proposed shelf life, quality and efficacy and/or texture or clumping of pharmaceuticals products. Of note, the United States Pharmacopoeia (USP) Method <1112> [Application of Water Activity Determination to Nonsterile Pharmaceutical Products] indicates that, measurements of the water activity may provide an accurate window into the quality microbial safety of pharmaceutical products.

Measurements of water activity are typically done by an indirect method such as by placing a sample in a closed chamber, allowing it to come to equilibrium, and measuring the water vapor pressure of the air over the sample. The water activity can be expressed as the ratio of this sample vapor pressure to the vapor pressure of pure water at the same temperature.

Water activity measurements can be carried out using instruments which uses chilled mirror dewpoint technology, instruments which utilizes relative humidity sensors that change electrical resistance or capacitance, as detailed in the Official Methods of Analysis of AOAC International (1995), or by any other manner known in the art.

The term "dried", as used throughout this specification, refers to a fibrin coating from which water has been removed. According to the invention the dried coating comprises some residual water contained therein. The term "residual water" refers to a coating comprising a water content in the range of about 3 to 20% by weight based on the total weight of the dried stabilized coating composition.

The water content in the coating can be equal to or less than 20% such as equal to or less than 15%, 14% or 10%. Alternatively, it is possible that the coating is in a substantially dry form having a water content of equal to or more than about 3%.

When using salt, the salt content in the stabilized fibrin coating can be equal or more than 60% and equal or less than 65%. In another embodiment of the invention the salt content is equal or more than 26% and equal or less than 28%. Still in another embodiment of the invention, the salt content is equal or more than 51% and equal or less than 68%. Still in another further embodiment of the invention, the salt content is equal or more than 20% and equal or less than 32%. Yet in another embodiment of the invention, the salt content is equal or more than 5% and equal or less than 8%. The water content in the dried fibrin coating can be equal or less than 20%. In another embodiment of the invention, the water content is equal or less than 10% and equal or more than 3%. The protein content in the stabilized coating can be equal or more than 30%, for example, up to 32%. In another embodiment of the invention the protein content is more than 64% and less than 69%. In another further embodiment of the invention, the protein content is 29%. Yet in another further embodiment of the invention, the protein content is more than 60% and less than 65%.

For example, the substrate can be coated with a concentrate of proteins containing fibrin under conditions in which the total amount of water is more that 3%, salt is equal or more than 20% and the content of protein is 77% or less. In another embodiment of the invention, the salt content is equal or more than 60%, the water content is less than 10%, and the protein content is equal or more than 30%. Yet, in another embodiment of the invention, the salt content is less than 65%, the water content is more than 3%, and the protein content is 32% or less. In another further embodiment of the invention, the salt content is less than 28%, the water content is more than 3%, and the protein content is less than 69%. Still, in another embodiment of the invention, the salt content is more than 26%, the water content is less than 10%, and the protein content is more than 64%. Yet, in another embodiment of the invention, the salt content is less than 68%, the water content is more than 3%, and the protein content is 29% or less. Yet, in another further embodiment of the invention, the salt content is more than 51%, the water content is less than 20%, and the protein content is more than 29%. Still in another further embodiment of the invention, the salt content is less than 32%, the water content is more than 3%, and the protein content is 65% or less. Yet, in another further embodiment of the invention, the salt content is more than 20%, the water content is less than 20%, and the protein content is more than 60%. In another further embodiment of the invention, the salt content is more than 5%, the water content is less than 20%, and the protein content is more than 75%. All percentages are by weight based on the total weight of the dried stabilized coating composition where the substrate weight is not taken into account.

It has been reported that surgery-related complications include adhesions such as visceral adhesions that may lead to bowel obsruction, pain, hernia recurrence, bacterial contamination and/or surgical site infections which may be developed into a chronic fistula that has to be operated.

It was reported that fibrin on prosthetic device can promote bacterial infection (Loike et al. U.S. Pat. No. 5,843, 436; and Mehall et al. "Fibrin sheath enhances central venous catheter infection". Crit. Care Med. 2002; 30:908-912). Surprisingly, it was found according to the invention that using stabilized fibrin on a substrate prepared according to the invention resulted in a reduction in the bacterial load to the coated device. Advantageously, including the fibrin coating reduce bacterial colonization of commonly found bacterial pathogens.

The efficacy of the device according to the invention in reducing surgically related complications can be assessed in an animal model, such as in the Abdominal Wall Defect Model as exemplified below. For example, in the abdominal wall defect model, a defect can be created through the membrane lining the abdominal cavity, i.e. the peritoneum, and also through a part of the abdominal muscle, and a mesh can be applied intraperitoneally to the created defect for different periods of time such as for up to 30 days. The results obtained indicate that spraying fibrin sealant onto the surface of a mesh placed within the surgery area resulted in a lower adhesion level as compared to an un-coated mesh. However, applying a fibrin sealant onto a mesh placed within the surgery area is time consuming, complicated and can result in a low amount of fibrin glue applied to the surface of the mesh due to dislodging of the applied material. Advantageously, it was also shown that using a pre-coated and wet fibrin sealant mesh was more efficient in adhesion reduction as compared to spraying the fibrin sealant onto a mesh which is placed in the surgery area during surgery. Advantageously, forming a pre-coated fibrin sealant mesh enables to use a relatively low concentration of fibrinogen activators, such as thrombin or snake venom e.g. Batroxobin, lowering exposure of the surrounding of the implant to the activator. Low concentrations of activators also generate thick fibrin fibers that can enhance the physical properties of the fibrin coating. In addition, the process of fibrin formation can be carried out for an extended period of time allowing full cross linking of the fibrin further contributing to the tensile strength of the fibrin coating. The increase in physical properties such as tensile strength is essential for surgical implants that have the task of bridging between tissues and organs.

Advantageously, the device according to the invention comprises a substrate pre-coated with dried fibrin that may be stored for extended periods of time before use. It has been found, surprisingly, that using the device prepared according to the invention can decrease the likelihood of postoperative complications such as infection and bacterial contamination of the coated device and prevent adhesions particularly adhesions involved with the intestine as compared to other devices. It was also found that the non visceral surface of the device enables tissue infiltration and integration of the device with the host-tissue. Advantageously, the integration of the device with the host-tissue affixes the device thereby significantly reducing the risk of opening or defect recurrence and reducing the postoperative pain.

To evaluate the efficacy of the implantable device of the invention in reducing the severity of adhesions a numerical score can be assigned. In this regard, the density of the adhesions and/or the percentage of the surface of the device involved with adhesion can be evaluated. The density of the adhesion can be graded from 0 to 3 according to Smith et al. (as specified in: Kayaoglu et al. "Comparison of adhesive properties of five different prosthetic materials used in hernioplasty". J Invest Surg. 2005; 18:89-95). While the grade 0 describes no adhesions; and the grade 3 describes dense bowel adhesions to the mesh. The density of the adhesions can also be categorized from 0 to 3 as specified in Toosie et al. 2000; the grade 0 describes no adhesion, and the grade 3-highly inseparable adhesions, requires sharp instruments for separation.

The percentage of the device coverage by adhesion formation can be determined by using a surface area grid and rounding off to the near 5 percent as described in Toosie et al. (2000), or as devised by Diamond et al. which relate to five possible categories that describe the severity of the adhesion (grade 0-4) (as specified in: Kayaoglu et al. 2005). The grade 0 describes no adhesions; and the grade 4 describes>75 coverage percentage.

The term "substrate" refers to any medical device or medical implant having one or more surfaces to which a "coating" may be applied. It also includes medical devices introduced into an organism. The substrate comprises a visceral oriented surface and a non-visceral oriented surface. The substrate used may be formed of any biocompatible material including plastic, silicone, metallic or non-metallic substances. The substrate used can be porous and/or non-porous. In one embodiment of the invention, the substrate comprises a plurality of open pores or void spaces. The pores can be in the range of from about 10 to about 3200 microns. In one embodiment of the invention, the pores are from about 1000 to about 1600 microns. The substrate can be inert. The substrate can be flexible. The substrate can be in various sizes and/or textures. In certain embodiments, if required, the substrate can be stiff in order to avoid compression and/or distortion during use. In one embodiment of the invention, the substrate is flexible and allows rolling, so it can be delivered into the surgical site through a narrow lumen in a folded form and then unbend in the site of surgery. In one embodiment of the invention, the substrate is not degradable.

As used herein, the term "visceral surface" refers to the exterior boundary of the substrate facing the patient's internal organs in use, and the term "non-visceral surface" refers to the exterior boundary of the substrate facing the interior cavity of the damaged tissue. The term visceral surface herein is interchangeable with the term extra-luminal surface. According to the invention the fibrin coating will be formed on at least a portion of the visceral surface of the substrate. Accordingly, the implantable device of the invention comprises a non-visceral surface adapted to be surgically adhered to the interior cavity of the damaged tissue and a visceral surface characterized by non-adhesion properties which in use will face the patient's internal organs. In one embodiment of the invention, the visceral surface is the portion of the surface which faces away from the fascia defect and the non-visceral surface is the portion which faces towards the defect. Thus, in one embodiment of the invention, the device according to the invention strengthens and/or repairs the fascial tissue.

The term "coated surface" means that the visceral surface of the substrate is at least partially coated with a stabilized fibrin coating to obtain a surface that will reduce the adhesion level between the visceral organs and the device of the invention. Of note, during the coating step residual amounts of the coating material can also contact the non-visceral surface of the device consequently resulting in the presence of a fibrin coating also on the non-visceral surface of the device. In that matter, the coated portions are such that do not interfere with tissue infiltration and integration of the device with the host-tissue.

Examples of suitable substrates according to the invention include, but are not limited to, pacemakers; stents e.g. vascular, gastroenterology, ureteric or urethral stents; orthopedic prostheses; silicone implants such as silicon breast; sutures; staples, catheters; artificial heart valves; meshes; and pumps.

In one embodiment of the invention, the substrate is a mesh. In such an embodiment the mesh to be used according to the invention can be made of synthetic or semi-synthetic material, including plastics and other polymers. Materials useful for making meshes include, but are not limited to, poly(ethylene); polyesters; poly(propylene), poly(propylene) polyesters such as poly(propylene) fumarate; polystyrene; polytetrafluoro ethylene (PTFE); nylon; polypropylene/cellulose; polypropylene/PTFE; polypropylene/monochryal; polyester/collagen; poly(acrylate); poly (methyl methacrylate); poly(hydroxy ethyl methacrylate); poly(vinyl alcohol); poly(carbonate); poly(trimethylene carbonate); poly(ethylene-co-vinyl acetate); poly(ester urethane); poly(ether urethane); poly(arylate); poly(imide); poly(anhydride-co-imide); poly(amino acid); polydepsipeptide; poly(phosphazene); poly(glycolic acid); poly(lactide-co-glycolide); poly(lactic acid); poly(ε-capro lactone); poly (p-dioxanone); poly(lactide-co-glycolide); poly(ε-caprolactone-co-glycolide); poly(glycolide-co-trimethylene carbonate); lactide/tetramethylglycolide copolymer; lactide/trimethylene carbonate copolymer; lactide-δvalerolactone copolymer; poly(lactide)/polyethylene oxide copolymer; lactide (ε-captrolactone copolymer); unsymmetrically 3,6-substituted poly(1,4-dioxane-2,5-dione); poly(β-alkanoic acids) such as poly(β-hydroxybutyrate)/(β-hydroxyvalerate) copolymer, poly(β-hydroxybutyrate), poly(β-maleic acid) and poly β-hydroxypropionate), poly(β-valerolatone); methylmethacrylate-N-vinyl pyrrolidone copolymer, polyesteramide; polyesters of oxalic acid; polydihydropyran; polyalkyl-2-cyanoacrylate; cellulosic materials; composites thereof; and combinations thereof. In one embodiment of the invention, the mesh to be used is made of polypropylene. Also, any of the currently marketed mesh products can be used including, but not limited to, Mersilene (Ethicon), Prolene® (Ethicon), SURGIPRO™ (Tyco), C-OUR™ (Atrium), Marlex (Bard), DUALMESH®, (Gore), DynaMesh® (FEG Textiltechnik), TiMesh (GfE), and PARIETEX® (Tyco). The fibrin can coat the mesh partially or completely. The thickness of the mesh can be sheet like. In another embodiment of the invention the thickness of the mesh to be used is 0.3±0.2 mm.

The implantable device according to the invention can be used for preventing, treating, ameliorating, correcting and/or reducing the symptoms of any medical condition. The device of the invention can be utilized to replace, augment and/or to facilitate the repair of a damaged tissue in any medical application such as support or reinforcement of soft tissue, reconstruction of soft tissue deficiencies, or for tissue and organ replacement such as for the repair of an aperture and/or defect in a tissue such as fascia tissue defects. Examples of such application include, but are not limited to, hernias, recurrence of hernias, chest wall defect and sealing of internal wounded tissue such as repair of a damaged blood vessel. It is also suitable for use in soft tissue defects resulting from extirpative tumor surgery. In one embodiment of the invention, the substrate is designed for intraperitoneal placement.

Uncomplicated hernias are typically repaired by returning the herniated tissue or organ to its original and correct position, and then repairing and reinforcing the weakness in the muscle tissue.

The term "hernia" relates to any protrusion of a tissue, structure, or part of an organ through the muscular tissue or the membrane in which it is normally contained. Usually, hernia occurs as a result of an opening, weakening, bulging or tearing of the muscular structure of the wall of the abdomen. Examples include, but are not limited to, incisional hernia, ventral hernia, hiatal hernia, postoperative hernia, epigastric hernia, spiegelian hernia, umbilical hernia, indirect or direct inguinal hernia, femoral hernia, diaphragmatic hernia, and generally any abdominal wall related hernia.

In vascular applications, the coated implantable device according to the invention will be applied is such a manner that the coated surface will be outside the extra-luminal surface of the implanted blood vessel. The coated surface enables to substantially reduce contact of the device with the visceral organs of the patients thereby providing a barrier between the device and the internal organs.

Advantageously, the visceral side of the device is coated with a stabilized fibrin coating to physically separate the device from adjacent tissue and organ surfaces in order to minimize tissue attachment to the device. The coating can completely cover the visceral side of the device and create a smooth surface on one side of the device, providing a tissue-separating layer between the device and the visceral cavity.

Implanted medical devices may trigger a series of biologic reactions, referred to herein as foreign body reactions. Typically, a foreign body reaction is characterized by an accumulation of inflammatory and fibrotic cells that adhere to the surface of the implant. Advantageously, the implantable prosthetic device of the present invention comprises the stabilized fibrin coating on the visceral side which provides a non-immunogenic-separating layer between the device and the visceral cavity. The term "prosthetic" refers to a substitute for a damaged or missing body part.

The results obtained according to the invention show that the non-coated side of the device allows integration of the device with the host-tissue. Without being bound by the mechanism, it is believed that the uncoated surface induces a prompt fibroblastic response ensuring prompt fixation and integration with the tissue through the interstices of the device.

In contrast to other composite meshes, the device according to the invention shows good performance in the presence of bacterial contamination. For example, implantation of the device according to the invention in a contaminated in vivo model resulted in reduction of the adhesion level and/or in prevention of infection as compared to a mesh covered with an oxidized regenerated cellulose (ORC) fabric; thus, the implantable device can be effectively used even in contaminated or potentially contaminated surgical areas. "Contaminated area" refers to a non sterile environment. The term "composite" refers to a device which is composed of different elements. In one embodiment of the invention, the device is composed of a synthetic polypropylene mesh and a coating of stabilized fibrin. In another embodiment of the invention, the mesh provides the mechanical strength that reinforces the defect tissue, serves as a matrix for the fibrin coating and enables optimal tissue in-growth. In another further embodiment of the invention, the stabilized fibrin coating decreases intra-peritoneal tissue and organ attachment to the mesh and reduces bacterial colonization of the mesh. In another further embodiment of the invention, the synthetic mesh is integrated with the host-tissue by the time the fibrin coating is digested in the body.

In contrast to biological implants, the use of the composite mesh according to the invention in hernia repair (also known as hernioplasty or herniorrhaphy) results in fewer long-term recurrence of hernia. "Biological implants" refers to a medical device of biological origin which is inserted into, or grafted onto, bodily tissue which may generally serve as a temporary tissue substitute and a template for new tissue formation.

The device according to the invention can be used as is, or can be re-hydrated before use. In one embodiment of the invention, the device is re-hydrated in a sterile saline solution prior to use. The device can comprise additives such as a coloring agent.

The device can also comprise anti-microbial agents and/or antibiotics including, but not limited to, heavy metals such as silver, chlorohexidine or other anti-microbial chemicals used clinically.

It was also found according to the present invention that the fibrin coating according to the invention reduces the bacterial load to the device.

The implantable device can be delivered to the desired location by any means used by surgeons for repair of defects including, but not limited to, open surgery, and minimal invasive procedure (MIS) such as laparoscopy. In one embodiment of the invention, an incision is made at the site of surgery and the implantable device is applied onto the defect. The patient can receive local, regional or general anesthesia.

The term "open surgery" refers to surgery wherein the surgeon gains direct access to the surgical site by a relatively large incision.

As used herein the term "minimally invasive procedure" means a surgery wherein the surgeon gains access to the surgical site via small incisions or through a body cavity or anatomical opening e.g. via laparoscopy. The device can be collapsible, e.g. by rolling, so it can be delivered into the surgical site through a narrow lumen in a folded form and unbend in the site of surgery due to its ability to resume it shape after deformation. Specialized techniques can be used to visualize the operated area such as, miniature cameras with microscopes, tiny fiber-optic flashlights and high definition monitors. Instruments having "end effectors" such as forceps, cutters, needle holders, cauterizers, and the like, can be introduced to the surgical site. In one embodiment of the invention, the device allows easy folding and de-folding when introduced via a trocar in laparoscopic surgery.

The device according to the present invention has at least one of the following advantages: increased anti adhesive properties on its visceral surface, resistance to bacterial colonization, reduced foreign body reaction on the visceral side, facilitates healing of the host-tissue, is sufficiently flexible to be easily conformed to the shape of the body surface and/or to be easily delivered during laparoscopic procedure, retains tensile strength within the body to avoid over-stretching of the weakened tissue, does not require special storage and has a long-term stability under prolonged storage, attaches to facial side when pressed wet, becomes an integral part of the host-tissue on the non visceral side of the device, is ready for use, and can be manufactured in various sizes and shapes. The device of the invention can be used in laparoscopic surgery. In one embodiment of the invention, the fibrin coating is transparent and allows visualization of the underlying tissue. The device according to the invention can be integrated into the tissue after a few days.

Subject matter of the present invention embraces a method for producing an implantable device for repairing an opening or a defect in a soft tissue, the method comprising the steps of: providing a substrate having a visceral surface and a non-visceral surface; forming a fibrin coating on at least a portion of the visceral surface by applying a defined volume of a solution comprising fibrinogen and a solution comprising a proteolytic enzyme which is capable of forming fibrin when it reacts with fibrinogen to the desired portion; and drying the coating, thereby obtaining an improved implantable device comprising a stabilized fibrin coating.

The term "improved implantable device" relates to an implantable device displaying reduced postoperative complications after its implantation. In one embodiment of the invention, the postoperative complications are selected from the group consisting of bacterial contamination, adhesions, infections, hernia recurrence and a combination thereof.

Typically, a fibrin coating is formed when fibrinogen and a proteolytic enzyme solution are mixed. Factor XIII, is typically present in the formulation for cross-linking of the fibrin monomers.

In one embodiment of the invention, the proteolytic enzyme is a solution obtainable from snake venom. In another embodiment of the invention, the proteolytic enzyme is thrombin. The fibrinogen used in the practice of this invention includes any fibrinogen that will form fibrin.

The fibrinogen and thrombin can be prepared from initial blood composition. The blood composition can be whole blood or blood fractions, i.e. a product of whole blood such as plasma. Fibrinogen and thrombin can be autologous, human including pooled plasma, or of non-human source. It is also possible that the fibrinogen and the proteolytic enzyme are prepared by recombinant methods.

The aqueous thrombin solution typically comprises thrombin and calcium chloride. The concentration of thrombin can be in the range of from about 2 to about 4,000 IU/ml, or in the range of from about 800 to about 1200 IU/ml. Calcium chloride concentration in the solution can be in the range of from about 2 to about 6.2 mg/ml, or in the range of from about 5.6 to about 6.2 mg/ml, such as in the concentration of 5.88 mg/ml. The thrombin solution may also comprise excipients. As used herein the terms "excipient" refers to an inert substance which is added to the solution. Examples of excipients include, but are not limited to, human albumin, mannitol and sodium acetate. The human albumin in the solution can be in the range of from about 2 to about 8 mg/ml. Mannitol can be in the concentration range of from about 15 to about 25 mg/ml. Sodium acetate can be added to the solution in the range of from about 2 to about 3 mg/ml.

In one embodiment of the invention, the fibrinogen component is comprised from a biologically active component (BAC) which is a solution of proteins derived from blood plasma which can further comprise tranexamic acid and arginine or lysine or mixtures of arginine and lysine, or their pharmaceutically acceptable salts. BAC can be a blood derived cryoprecipitate, in particular concentrated cryoprecipitate. The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of a precipitate that contains fibrinogen and factor XIII. The precipitate can be collected, for example by centrifugation. The solution of BAC comprises further Factor VIII, fibronectin, von Willebrand factor (vWF), vitronectin, etc. Example of such BAC is disclosed in U.S. Pat. No. 6,121,232 and WO9833533. Typically, the amount of fibrinogen in BAC is in the range of from about 40 to about 85 mg/ml. The amount of tranexamic acid in the solution of BAC can be from about 80 to about 110 mg/ml. The amount of arginine hydrochloride can be from about 15 to about 25 mg/ml.

Optionally, the proteolytic enzyme and/or the fibrinogen component are buffered to a physiological compatible pH value. The buffer can be composed of glycine, sodium citrate, sodium chloride, calcium chloride and water for injection as a vehicle. Glycine can be present in the composition in the amount of from about 6 to about 10 mg/ml, the sodium citrate can be in the range of from about 1 to about 5 mg/ml, sodium chloride can be in the range of from about 5 to about 9 mg/ml and calcium chloride can be in the concentration of about 0.1-0.2 mg/ml.

In another embodiment, the concentration of plasminogen and plasmin in the BAC composition is lowered to equal or less than 15 µg/ml like for example 5 mg/ml or less plasminogen using a method as described in U.S. Pat. No. 7,125,569, EP-B-1,390,485 and WO02095019. In another embodiment of the invention, when the concentration of plasminogen and plasmin in the BAC composition is lowered the composition does not contain tranexamic acid.

It is also possible that the proteolytic enzyme solution and/or the fibrinogen component comprises components which encourage the formation of the clot such as, but not limited to, $Ca^{2+}$, Factor VIII, fibronectin, vitronectin, and von Willebrand factor (vWF).

Components derived from blood compositions can be treated to reduce and/or inactivate infective particles. This can be carried out by different methods such as, but no limited to, filtration, solvent/detergent treatment, heat treatment, such as pasteurization, gamma or UVC (<280 nm) irradiation, or by any other method known in the art. The term "infective particle" refers to a microscopic particle such as, but not limited to, microorganism or a prion, which can infect or propagate in cells of a biological organism. The infective particles are for example viral particles.

The inactivation procedure of infective particles can be carried out by adding an inactivating molecule to the composition prior to and/or during the procedure. The added molecules and their products can be removed by gravitation, column chromatography or by any other method known in the art.

The removal of infective particles can be carried out by filtration or by selective absorption methods such as affinity, ion exchange or hydrophobic chromatography. A multi-step viral inactivation procedure can be carried out. For example, the composition can be subjected to solvent/detergent treatment, heat treatment, selective chromatography and filtration.

The surface of the substrate can be activated prior to the coating step to enhance wetting of the surface by the coating solutions, to increase the adhesive force between the coating solutions and the surface of the substrate and/or to aid with cellular attachment on the non-visceral side of the device consequently facilitating tissue infiltration and integration of the device with the host tissue. Methods of surface activation include, but not limited to, plasma treatment such as cross-linking by activated species of inert gases, plasma deposition, plasma etching and plasma cleaning; corona discharge; chemical modifications of the surface such as chemical attack with acidic liquids; modification by exposure to gamma irradiation in the presence of a reactive gas; and combinations thereof. In one embodiment of the invention, the surface of the substrate is subjected to plasma treatment prior to forming the fibrin coating.

The substrate can be coated by any of the methods known to one of ordinary skill in the art. For example, physical adsorption, dipping the substrate in the coating material, pressing the substrate against a roller saturated with the coating material, passing the substrate through rollers that transfer the coating onto the surface of the substrate, passing the coating material through a slot onto the surface of the substrate, or by using a brush or spraying the substrate with the coating material. The substrate can also be sprayed with microdroplets and nanodroplets. Homogenous distribution can also be achieved by using a drip on apparatus or an applicator comprising at least one jet or by using a dispenser such as by using the BioSpot® coating machine manufactured by BioFluidix which enables to control the coating volume through the surface of the substrate. This technology enables the non contact dispensing of liquid droplets in the range from a few nanoliter up to some microliter. The coating material can completely or partially cover the visceral surface of the device and create a substantially smooth film. To selectively coat only a portion of the substrate the coating material can be deposited through a template that exposes only the desired areas of coverage for the coating.

The substrate can be coated with fibrinogen and the proteolytic enzyme either simultaneously or one after the other. In one embodiment of the invention, the fibrinogen is first applied to the substrate followed by application of the thrombin.

The components may be mixed in any desired range of ratios. For example, when the concentration of the fibrinogen component is 40-85 mg/ml and the thrombin concentration is about 800-1200 IU/ml the two components can be mixed in a ratio of 1:1, 1:0.5, 1:0.3, 1:0.25, 1:0.1, 1:0.05, respectively, and so on.

Any non-intensive drying known in the art that does not deteriorate the coating and the substrate can be used. The term "intensive drying" is for example lyophilization (freeze drying) or spray drying procedures. The drying can be carried out at different temperatures using various drying equipments, such as controlled humidity chamber, drying oven, drying tunnel, vacuum drier, or in any other suitable method which does not affect the coated device. Alternatively, the applied coating can be air dried. In one embodiment of the invention, the substrate is sensitive to thermal procedures. In another embodiment of the invention, the temperature during the drying step is lower than 37° C.

Generally, air drying at air room temperature achieves a relatively gradual decrease in the water content resulting in an increased stabilization of the fibrin coating. While not wishing to be bound by any theory, the enzymatic action of fibrin formation and cross-linking of fibrin monomers continuous gradually during the air drying process consequently resulting in a cross-linked and stabilized fibrin coating having an increased adherence to the surface of the substrate.

As used herein, the term "air dried" refers to drying at air room temperature at ambient atmosphere conditions. "Room temperature" means a temperature of less than 37° C. and above the freezing point of water such as about 15° C. to about 25° C. In one embodiment of the invention, the humidity of the atmosphere during air drying is of about up to 60% such as in the range of about 40-55%. The desired environmental conditions can also be obtained by using an environment control device such as a humidifier/dehumidifier set to the above listed temperature and humidity conditions. The conditions for drying such as humidity, time, pressure and temperature are selected to obtain a water content of less than 20% such as in the range of about 3 to 20%, less than 15%, less than 10% or more than about 3% by weight based on the total weight of the dried stabilized coating composition.

In one embodiment of the invention, the coating is air dried for 8 to 24 hours at humidity of 50-60% and at a temperature of about 25° C. In another embodiment of the invention, the coating is dried at a humidity of 60% and at a temperature of about 25° C. which are defined as Climatic Zone II condition by the World Meteorological Organization (WMO).

Following the drying step, the thickness of the coating is reduced. The thickness of the fibrin coating following drying can be in the range of from about 10 to about 1000 microns.

Advantageously, a solute capable of binding free water having a molecular weight of about 1,000 Dalton or less can be added to increase stability of the coating. The inclusion of said solute can be carried out before or after the fibrin is generated. In one embodiment of the invention the solute is added after the fibrin is formed. In this regard any solute can be used. The solute incorporation, after the formation of the clot, can be carried out in any of the methods known in the art such as physical adsorption, dipping, diffusion, pressing the fibrin-coated device against a roller saturated with the solute, passing the fibrin-coated device through rollers that transfer the solute onto the device, passing the solute through a slot onto the surface of the substrate, or by using a brush or spraying the fibrin-coated device with the solute. Alternatively, a drip on apparatus or an applicator comprising at least one jet or a dispenser such as BioSpot® coating process can be used.

Alternatively, the fibrin is formed in the presence of said solute. Since fibrin is formed by an enzymatic reaction addition of chemical substances to the fibrin-forming components may affect thrombin clotting activity or clot formation. Thus, when the fibrin is formed in the presence of said solute the solute and the concentration used should be permissive to the activity of thrombin or to any other enzyme capable of forming fibrin when it reacts with fibrinogen, or to any enzyme involved in the polymerization of fibrin such as factor XIII.

In one embodiment of the invention, the chemical properties of said solute, if present during clot formation, permits retaining from about 50 to about 100% of the enzyme clotting activity compared to the activity in the absence of the solute, i.e. the remaining enzyme clotting activity following addition of the solute is in the range of from about 50 to about 100% of the initial activity. In another embodiment of the invention, the remaining clotting activity after addition of the solute is in the range of from about 90 to about 100%. In another further embodiment of the invention, tranexamic acid salt is used.

The solute can be included in the proteolytic enzyme e.g. thrombin, in the fibrinogen component, and/or can be as a separated component.

Examples of solutes include, but are not limited to, amino acids such as tranexamic acid, arginine hydrochloride, lysine hydrochloride and salts thereof; salts such as calcium chloride, potassium chloride, sodium chloride, tri-sodium citrate; saccharides such as sucrose and maltose; polyols such as polyglycerol; sugar alcohols such as mannitol and xylitol and a combination thereof.

Yet another object of the invention is to provide a kit comprising a first container comprising an implantable device according to the invention, and a second container comprising a re-hydration solution. The kit can also contain instructions to the physician, or the health care professional for its use. The re-hydration solution can be water and/or salts such as saline. The re-hydration solution can be provided in a vial or a pre-filled syringe.

It is another object of the invention to provide a method for repairing an opening or a defect in a soft tissue in a patient in need, the method comprising the steps of: providing an implantable device according to the invention, and applying the device of the invention adjacent said opening and/or defect. The device of the invention can be applied with the coated surface facing the visceral organs and the un-coated surface facing the opening and/or defect. In one embodiment of the invention, the opening and/or defect is a hernia as defined above. In another embodiment of the invention, the device is re-hydrated prior to application of the device.

The term "adjacent" means that the device can be applied in such a manner that substantially all of the opening and/or the defect are covered.

The implantable device can be sterilized prior to implantation. Alternatively, the device of the invention can be supplied in a sealed sterile package which enables removal of the device without contamination. Any appropriate sterilization method known in the art that does not deteriorate the device, such as melting of the substrate can be used.

When performing abdominal wall repair the device can be attached to the inner face of the abdominal wall, e.g. the fascia of the patient. Alternatively, the device can be attached to the peritoneum. In one embodiment of the invention, the device is attached to the peritoneum of the patient.

The device can be fixed to the desired location through the use of sutures, staples or by similar means. Alternatively, the device can be anchored by using a tissue adhesive. The device can be attached around its entire perimeter or by opposite and in-diagonal relationship.

The implantable-device of the invention can be prepared and provided in a variety of sizes and shapes such as circular, polygonal, spherically, conically, cubically, oval, rectangular or cylindrically, depending on the intended use. The device of the invention can be sized to extend beyond the defect or the opening. The device of the invention can be flat, planar, concave, and/or convex. In one embodiment of the invention, the device is a mesh comprising a coating of stabilized fibrin. In another embodiment of the invention, the stabilized-fibrin coated mesh has a flat rectangular shape and is provided in the following sizes: 5×10 cm, 10×15 cm, 15×20 cm, 15×30 cm, 20×20 cm, 20×25 cm, 30×30 cm or 40×40 cm.

The disclosure of applications, patents and publications, cited above or below, is hereby incorporated by reference. The features, aspects, and advantages of the present invention will become better understood with regard to the following description, examples, claims, and the figures.

EXAMPLES

Materials and Methods

Fibrin Sealant Compositions:
BAC1 composition. 40-60 mg/ml concentrate of human fibrinogen; 85-105 mg/ml tranexamic acid; 17.0-21.0 mg/ml arginine hydrochloride; 7.2-8.6 mg/ml glycine; 2.4-2.9 mg/ml sodium citrate; 6.9-7.1 mg/ml sodium chloride; 0.14-0.16 mg/ml calcium chloride; at pH=6.7-7.2.

BAC2 composition. 55-85 mg/ml concentrate of human fibrinogen; 17.0-21.0 mg/ml arginine hydrochloride; 7.2-8.6 mg/ml glycine; 2.4-2.9 mg/ml sodium citrate; 6.9-7.1 mg/ml sodium chloride; 0.14-0.16 mg/ml calcium chloride; at pH=6.7-7.2.

Thrombin composition. 800-1200 IU/ml thrombin; 5.6-6.2 mg/ml calcium chloride; 5.0-6.5 mg/ml human albumin; 18.5-20.5 mg/ml mannitol; 2.5-2.7 mg/ml sodium acetate; at pH=6.8-7.2.

Freeze Drying Procedure. The freeze drying procedure was carried out as follows using the CHRIST, EPSILON 2-8D Freeze Dryer: The temperature was lowered to −45° C. for 2 hours. Afterwards, the temperature was kept at −50° C. for a period of 5 hours. This step was followed by sublimation at a temperature of −15° C. and at a pressure of 0.14 mbar for up to 24 hours. After that the temperature was increased to +25° C., pressure was reduced to 0.02 mbar and a secondary drying was carried out for up to 24 hours.

Vacuum Drying Procedure. Vacuum drying procedure was carried out in an oven (ShelLaB Model 1430-2E) set to room temperature at a pressure of 0.4 mbar or less for 2 hours unless indicated otherwise.

Quantification of Water Content. Water content determination was carried out using the volumetric Karl Fischer Titration method (KFT) which is based on the US Pharmacopoeia assay (USP 27, 921, P. 2398-2399).

The basis reaction of the Karel Fischer Titration can be expressed according to the following formula:

$$ROH+SO_2+RN \rightarrow (RNH).SO_3R(RNH).SO_3R+2RN+$$
$$I_2+H_2O \rightarrow (RNH).SO_4R+2(RNH)I$$

The alcohol reacts with sulfur dioxide and base to form an intermediate alkyl sulfite salt, which is then oxidized by iodine. This oxidation reaction consumes water in a 1:1 ratio.

The procedure is as follows: first, the water was extracted from the sample by placing a pre-weighed piece of the coated mesh (0.1-0.2 g) in a tube and adding about 15 ml dried Methanol (Merck cat No. 1.06012). The tube was then shaked for 30 minutes at room temperature. Then, about 4-6 ml from the supernatant was taken for the titration. The titration procedure was carried out by the automated titration system Mettler-Toledo-DL38 or Metrohm®. Briefly, Karl Fischer reagent (Hydranal, Composite 2, Riedel-de Haen cat No. 34806) which contains iodine is gradually added to the reaction until all the water present is consumed and the presence of excess iodine is electrically detected by the automated titration system. The detection of free iodine signals the end point of the titration. The amount of iodine added serves to calculate the amount of water present in the sample. The amount of added iodine is calculated according to the amount of Karl Fisher Reagent consumed in the titration and the concentration of iodine in the Karl Fischer reagent. The measurement was carried out in duplicates.

The water content of the dried methanol (20 ml) is tested and subtracted from the average water content result of the sample as follows:

The average result of the sample (%)–[the average result (%) of the dried Methanol×100 mg×the volume of the supernatant taken for titration]/(the relative test sample weight in mg*×20 ml).

*Equals the volume of the supernatant taken for titration multiplied by the pre-weighed piece of the coated mesh and divided by the volume of the dried Methanol added in the water extraction step.

Mesh Fabrics. Unless indicated otherwise, the following types of Polypropylene mesh fabrics were used: PPKM403, PPKM404, PPKM601 and PPMK602 manufactured by Textile Development Associates, Inc. The characteristics of the mesh fabrics are described in Table 1.

TABLE 1

The characteristics of the mesh fabrics.

| Style | Monofilament Dia. mm (in) | Typical Pore Size mm (in) | Burst Strength kPa (psi) | Break Strength N/2.5 cm (lbs/in) MD | Break Strength N/2.5 cm (lbs/in) CMD | Break Elongation (%) MD | Break Elongation (%) CMD | Thick. mm (in) | Wt. g/m² (oz/yd²) |
|---|---|---|---|---|---|---|---|---|---|
| PPKM403 | 0.10 (.004) | 1.4 × 1.1 (.055 × .043) | 592 (86) | 222 (50) | 210 (47) | 82 | 135 | 0.42 (.017) | 47 (1.4) |
| PPKM404 | 0.10 (.004) | 1.0 × 0.7 (.039 × .028) | 600 (87) | 138 (31) | 200 (45) | 151 | 110 | 0.38 (.015) | 44 (1.3) |
| PPKM601 | 0.15 (.006) | 1.3 × 1.0 (.051 × .039) | 1172 (162) | 526 (118) | 492 (111) | 107 | 175 | 0.59 (.023) | 100 (2.9) |
| PPKM602 | 0.15 (.006) | 0.8 × 0.6 (.031 × .024) | 862 (125) | 322 (72) | 427 (96) | 170 | 124 | 0.53 (.021) | 97 (2.9) |

Abdominal Wall Defect Model. Male Sprague Dawley albino rats of known bacteriological and viral status (Harlan Lab., Rehovot, Israel), weighing 250-350 g, were housed in an authorized facility according to the current ethical requirements. All animals were subjected to a clinical inspection upon arrival. The animals were caged and provided diet ad libitum and had free access to sterilized tap water. Before and after surgery, animals were housed in an air-conditioned room, in a temperature range of 22±4° C., relative humidity of 30-70% and under an artificial lighting cycle (12 hours artificial light/12 hours dark). The animals were randomly assigned to the different groups prior to surgery. Identification of animals was done by picric acid labeling.

Anesthesia: Rats were weighed before surgery and on the day of the autopsy Animals were anesthetized with 80 mg/kg IM injection of a mixture of 85/15 Ketamine HCl 100 mg/ml (Fort Dodge Pty. Ltd., Australia) and Xylazine HCl, 20 mg/ml (VMD, Belgium).

The rats were shaved at the surgical site and a 6 cm incision was marked on the skin overlaying the linea on the ventral midline. The skin was prepped with iodofor solution and incised. The skin was retracted and undermined slightly to facilitate suturing at the end of the procedure. With the muscle wall exposed, a 5 cm incision in the muscle was made along the linea all through the peritoneal cavity. The right abdominal wall was exposed. A 2×1 cm of the peritoneum was removed. The medial edge of this defect was located 1 cm lateral from the midline incision and parallel to it. The abdominal wall defect was exposed to air for 10 minutes to monitor any bleeding. Different variations of mesh fabrics were applied to the wounds in the manner specified below. The midline incision was closed with a running 2-0 Dexon™ II bi-color suture (Covidien syneture, USA) or with a running 3-0 Softsilk (Syneture, USA) and the skin was closed with the same suture so no bleeding occurs.

Mesh Application: In each rat, the mesh was applied on the abdominal wall defect and attached to the area by two opposite and in-diagonal sutures using 5-0 AssuCryl® MonoSlow suture (AssutSutures, Switzerland). In the case that the implantable device of the invention was surgically implanted, the coated surface was facing the visceral organs and the un-coated surface was placed while facing the abdominal wall defect. Following the mesh implantation the animals were monitored daily for assessing any irritation or pain signs.

The animals were kept without anesthesia after the procedure and were sacrificed at different time points during a period of up to 30 days. The animals were euthanized using $CO_2$ and a V-shape incision was made exposing the abdominal wall. The mesh was photographed and the degree of the adhesions and/or the integration level of the mesh with the surrounding tissue were assessed. The level of adhesion was assessed according to the scoring methodology described below and the integration level was assessed by resistance to isolate the integrated mesh from the tissue.

Determination of adhesion level. The adhesion level was evaluated according to one of the following scoring methodology:

| 1) Smith et al. and Diamond et al. methodology* | | |
|---|---|---|
| Adhesion Grading | **Smith et al. | ***Diamond et al. |
| 0 | No adhesions | No adhesions |
| 1 | Filmy adhesions | ≤25 |
| 2 | Definite bowel or omental adhesions | ≤50 |
| 3 | Dense bowel adhesions to the mesh | ≤75 |
| 4 | | >75 |

*Disclosed in Kayaoglu et al. "Comparison of adhesive properties of five different prosthetic materials used in hernioplasty". J Invest Surg. 2005; 18: 89-95)
**Density of adhesions
***Percentage of the surface of mesh involved with adhesion.

| 2) Toosie et al.* methodology | |
|---|---|
| Adhesion grading | Adhesion Density Scale |
| 0 | No adhesion |
| 1 | Low; adhesion easily removed |
| 2 | Moderate; difficult to separate adhesions |
| 3 | Highly inseparable, requires sharp instruments for separation of adhesions |

*Toosie et al. "Fibrin glue reduces intra-abdominal adhesions to synthetic mesh in a rat ventral hernia model". Am Surg. 2000; 66: 41-45.

Bacterial Colonization of the Mesh and the Underlying Tissue. This procedure was used when utilizing the abdominal wall defect as a model. The meshes were removed along with a thin layer of underlying abdominal wall tissue and stored at −80° C. until assayed. Half of each mesh was placed in a sterile test tube and vortex-washed with 1 ml PBS for about 10 sec. This step was carried out 5 times. The wash solutions of each animal were combined, serially diluted with PBS and spot-plated on TSBA+5% Def. Sheep Blood 90 mm petri dishes (HyLabs cat No. PD049). Bacterial colonies were counted after incubation overnight at 37° C. The results are expressed as colony-forming units (CFU) per $cm^2$ of mesh surface. Statistical analysis was performed using Student's T-test.

Subcutaneous model in Mice. Adult Female Swiss Webster mice (Mus musculus), weighing 20-35 g at study initiation, were purchased from Harlan Sprague Dawley, Inc. (Indianapolis, Ind.). Identification of animals was done by a number written with permanent marker on the tail. Animals were acclimated for a minimum of 3 days prior to the initiation of the study. The mice were weighed prior to the beginning of the surgery. Upon arrival, the mice were group housed in solid bottom caging at a target temperature of about 21° C. (18-26° C.) and a target relative humidity of 50% (30-70%), and maintained on an approximate 12 hour light/12 hour dark cycle. Following the surgery, the animals were housed individually. Animals were fed a diet ad libitum (5002-Purina certified rodent diet, PMI Nutrition) and municipal water or gel packs were provided ad libitum. The animals were handled and maintained in accordance with the Guide for the Care and Use of Laboratory Animals. The animals were observed at least once daily prior to study onset to determine their general health status based on food consumption, excretion and general behavior. Post-surgery, the animals were observed twice a day for 5 days for signs of pain and/or discomfort. Anesthesia: The animals were under general anesthesia during the implantation procedure. All mice were induced with isoflurane (3-5%) with an oxygen flow rate of 1-2 liters/minute via a charged induction chamber. Following anesthetic induction, the animals were removed from the induction chamber and received ophthalmic ointment in each eye. Anesthesia were maintained throughout the duration of the surgery via semi-closed circuit of isoflurane (1-4%) and oxygen (1-2 liters/minute) by mask while under a laminar flow hood or other waste gas evacuation system.

Analgesics: Animals received analgesics prior to start of surgical procedure in order to minimize any pain or distress (Buprenorphine hydrochloride; 0.1 mg/kg, SC). The average weight of all test animals were calculated for dosing of the analgesic. Following surgery, animals were observed for signs of pain and/or discomfort twice daily for a period of 5 days. Any animal that demonstrates any sign of pain and/or distress following surgery received additional analgesics (Buprenorphine hydrochloride; 0.05-0.1 mg/kg, SC). Analgesics were given based on the following "Parameters for the Evaluation of Pain": attempting to protect, move away, or bite; crying out when palpated or forced to use affected areas; licking, biting, scratching, shaking, or rubbing; pacing, lying down and getting up, or shifting weight; significant decrease in mobility; unusual length of time for recumbency; reluctance to move or difficulty in rising; and head down, tucked abdomen, hunched, facial distortion, or pallor.

Surgical Procedure. The entire back of the mouse from the dorsal scapular area to the dorsal lumbosacral area were clipped free of hair using electric animal clippers. The area was scrubbed with an aqueous iodophor solution, chlorhexidine diacetate and rinsed with alcohol. The anesthetized and surgically prepared mouse was delivered to a heated surgical board under a laminar flow hood, in sternal recumbency. Using sterile instruments for each mouse, bilateral incisions, approximately 1 cm lateral to the vertebral column and 1.5 cm in length, were made caudal to the scapula. The skin was then separated from the underlying connective tissue by creating two pockets measuring approximately 1.5×1.5 cm. The pockets were created approximately 1 cm from the skin incision. Care was taken to ensure that an intact tissue bridge will be left between the two skin incisions, in order to prevent migration of the implanted mesh and the bacteria between the two pockets. The different mesh fabrics were placed into the pockets. Following application of the different meshes the meshes were subjected to bacterial spiking. SURGISIS® meshes were subjected to 0.1 ml saline containing $3.3 \times 10^5$ CFU *Staphylococcus aureus* (ATCC 6538) and the stabilized fibrin coated meshes were subjected to 0.1 ml saline containing $4.4 \times 10^5$ CFU *Staphylococcus aureus*. Each animal was implanted with the same mesh in both created pockets. The skin incisions were closed with surgical wound clips or appropriate suture. Each tested group contained 6 animals. Mice were visually monitored for respirations throughout the procedure. The stability of the inoculum level was monitored during the implantation procedure Immediately after the completion of the surgical procedure, the mice were placed in a heated recovery container to retain body heat during this period. The animals were monitored until they were conscious and ambulatory and were then placed in their cages in the animal room.

The animals were euthanized at day 15 by inhalation of 100% carbon dioxide for no less than 2 minutes. After death has been confirmed using any appropriate method, the femoral arteries or other major blood vessel was transected as a confirmation of death. Following euthanizing, the skin on the back of each mouse was swiped with 70% alcohol and dried. The subcutaneous pockets were exposed and the following parameters were evaluated: 1) the bacterial count on the implanted mesh and the surrounding tissue; and 2) the inflammatory reaction level (infection score).

The evaluation was carried out as follows: The implant was harvested with approximately 2-3 mm of adjacent skin using sterilized instruments. The tissue and implant were placed in a sterile tube until assayed for bacterial count.

Bacterial count evaluation. The explanted mesh and tissue were immersed in 10 ml 0.85% saline with Tween 80 (2.5 mL/L) and lecithin (0.35 g/L) in a sterile tube. The tissue and implant were separated with sterile tools inside the tube (to allow better release of bacteria). The colonized bacteria was removed by sonication at 50 to 60 Hz for 10 minutes using a VWR Aquasonic 75HT with auxiliary tray. The homogenate was enumerated by agar pour plate methods using 0.85% saline with Tween 80 (2.5 mL/L) and lecithin (0.35 g/L) as dilution medium and TSA agar containing Tween 80 (2.5 mL/L) and lecithin (0.35 g/L). The plates were incubated at 37° C. for 48 hours and the bacterial colonies were counted. The average plate count from each group is reported as CFU per implant.

Inflammatory reaction. This parameter was evaluated by a visual inspection of the explant according to the following ranking: 1—No infection, explant flat, tissue looks healthy; 2—some infection, explant swollen, slightly necrotic; and 3—Sever infection, explants encapsulated, tissue necrotic.

Qualitative determination of the stability of the fibrin coating layer. Stability assessments were carried out by a visual inspection of the coating structure taking into consideration the continuity of the coating and the flakiness of the coating from the device.

Example 1: The Effect of Spraying Fibrin Sealant onto a Mesh Fabric Placed within the Surgery Area on the Adhesion Level Adhesions between tissues are undesired side effect in surgery. Fibrin sealant has been used in different experimental studies to decrease adhesion formation (Martin-Cartes et al. 2008; Toosie et al. 2000). Thus, in the following example the mesh was placed within the surgery area, fibrin sealant was sprayed onto the mesh surface and the adhesion level was evaluated 14 or 30 days following the mesh implantation. The Abdominal Wall Defect Model was used as described above. Uncoated mesh fabrics were used as control.

PPKM602 mesh fabric was cut to 1.7×2.7 cm pieces, placed in a molding device made of Teflon and autoclaved. The mesh fabrics were placed in the surgery site and sprayed with BAC1 and thrombin (for the composition see materials and methods). Equal amounts of these two components were used with a total volume of 0.3 or 0.6 ml.

Figure 1B:
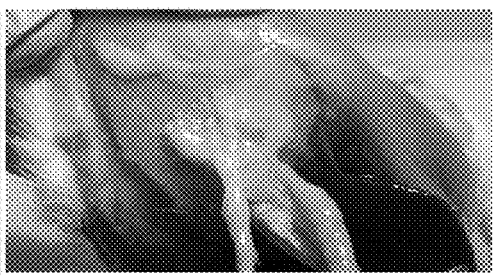

The postoperative adhesion grading following application of these mesh devices is summarized in Table 2 below. FIGS. 1 and 2 show the adhesion level in the surgery area in representative rats 14 and 30 days following surgery, respectively in control groups (A), 0.3 ml applied fibrin sealant (B), and 0.6 ml applied fibrin sealant (C).

TABLE 2

The anti-adhesion effect of a mesh coated with fibrin sealant at the site of surgery.

| Animal | Sample | Mesh (mg) | *FS (ml) | Days in vivo | **Adhesion grading |
|---|---|---|---|---|---|
| 1 | Mesh | 45.4 | — | 14 | 4 |
| 2 | Mesh | 46.7 | — | 30 | 4 |
| 3 | Mesh + FS | 48.5 | 0.3 | 14 | 3 |
| 4 | Mesh + FS | 41.9 | 0.3 | 30 | 2 |
| 5 | Mesh + FS | 44.0 | 0.6 | 14 | 2 |
| 6 | Mesh + FS | 47.2 | 0.6 | 30 | 1 |

*FS—fibrin sealant.
**The adhesion grading was assigned based on Smith et al. and Diamond et al. scoring methodology (see materials and methods).

The results obtained indicate that spraying fibrin sealant onto the mesh surface in situ resulted in a lower adhesion level as compared to the control group (uncoated mesh). After 30 days it was apparent that both volume coatings, i.e. 0.3 and 0.6 ml, showed a significant decrease in adhesion level as compared to the uncoated meshes.

Example 2: The Anti-Adhesion Effect of a Mesh Pre-Coated with Wet Fibrin Sealant The previous example shows the beneficial effect of applying fibrin sealant onto a mesh fabric placed within the surgery area in reducing adhesions in the operated area.

The present example was aimed to determine the anti-adhesive effect of a pre-coated and wet fibrin sealant mesh in surgery.

For this purpose, the PPKM602 mesh fabric was cut to 1.7×2.7 cm pieces, placed in a molding device and autoclaved. This step was followed by spraying the fibrin sealant components (BAC1 and thrombin in equal quantities) onto one side of the mesh fabrics (the total amount of the components are listed in Table 3 under FS). During the spraying procedure the mesh fabrics were placed in the molding device. The sprayed samples were incubated in the refrigerator (4° C.) for 3 days [the coated meshes were kept wet during storage because of the relative high humidity (80-95%) in the refrigerator]. Uncoated-autoclaved samples were used as control.

An in vivo evaluation of the effect of the wet fibrin pre-coated mesh fabrics on adhesion reduction and on the integration level of the mesh with the surrounding tissue was carried out using the Abdominal Wall Defect Model as described above. Twelve animals were used of which 6 served as controls and 6 were treated with the wet-pre-coated mesh. When applying the mesh into the rat, the uncoated side faced the defect.

The results obtained are presented in Table 3 below and in FIGS. 3-5. The Figs. show the adhesion degree and the integration of the mesh with the surrounding tissue of representative rats in the control group (A) as compared to the wet fibrin sealant pre-coated mesh fabrics (B) on the 15th (FIG. 3) and 30th day (FIGS. 4 and 5) following implantation. The operated area is circled.

TABLE 3

The anti-adhesion effect of a wet fibrin sealant coated mesh

| Animal | Sample | Mesh (mg) | Mesh + FS (mg) | FS (mg) | Days in vivo | *Adhesion grading |
|---|---|---|---|---|---|---|
| 1 | Mesh + FS | 44 | 614 | 570 | 15 | 1 |
| 2 | Mesh + FS | 44 | 505 | 461 | 15 | 1 |
| 3 | Mesh + FS | 44 | 532 | 488 | 6 | 4 |
| 4 | Mesh | 44.4 | — | — | 6 | 4 |
| 5 | Mesh | 44.7 | — | — | 15 | 4 |
| 6 | Mesh | 42.5 | — | — | 30 | 3 |
| 7 | Mesh | 44.7 | — | — | 30 | 3 |
| 8 | Mesh + FS | 44 | 445 | 401 | 30 | 0 |
| 9 | Mesh | 42.8 | — | — | 30 | 3 |
| 10 | Mesh + FS | 44 | 434 | 390 | 30 | 0 |
| 11 | Mesh | 43.5 | — | — | 30 | 3 |
| 12 | Mesh + FS | 44 | 583 | 539 | 30 | 0 |

*The adhesion grading was assigned based on Smith et al. and Diamond et al. scoring methodology (see materials and methods).

Figure 3A:
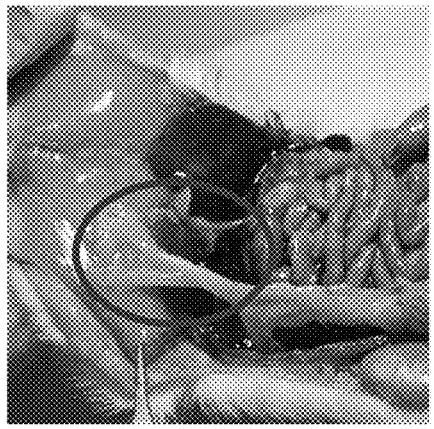
FIGS. 3-5 show the adhesion degree and the integration of the mesh with the surrounding tissue of representative rats in the control group (A) as compared to wet fibrin glue pre-coated mesh fabrics (B) on days 15 (FIG. 3) and 30 (FIGS. 4 and 5) following implantation (the operated area is circled).
Figure 3B:
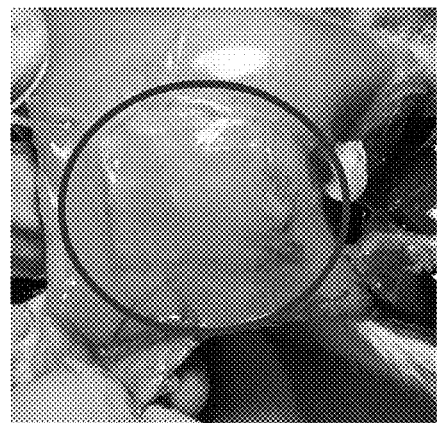
Figure 4A:
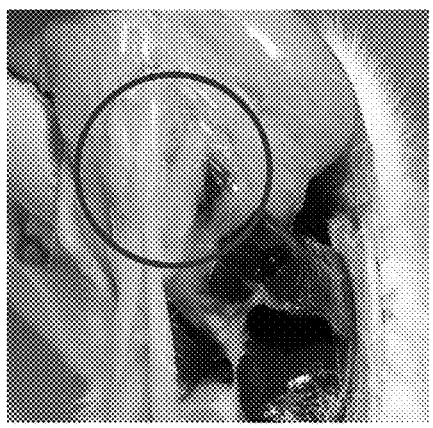
Figure 4B:
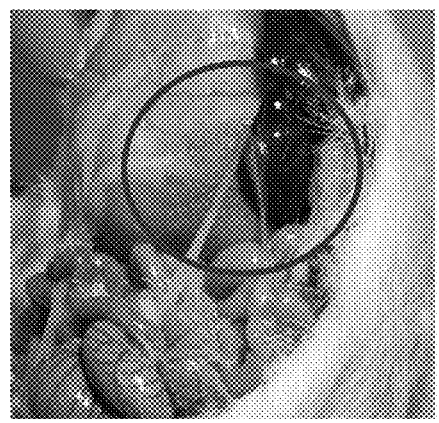
Figure 5A:
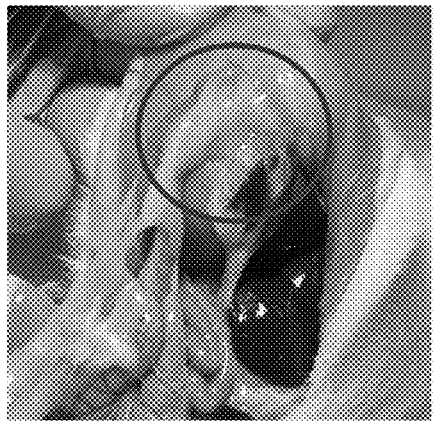
Figure 5B:
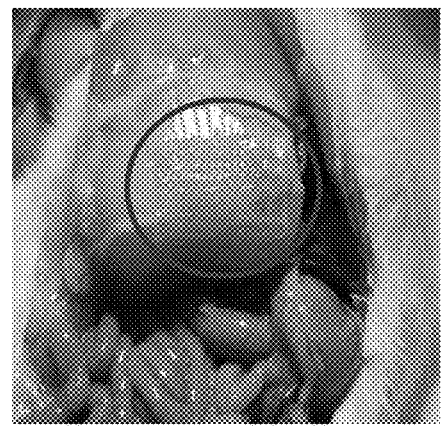

The results obtained show that a wet fibrin sealant pre-coated mesh led to a significant decrease in the adhesion level in the visceral side as compared to an uncoated mesh fabric (Table 3 and FIGS. 3-5).

In addition, a wet fibrin sealant pre-coated mesh resulted in a better tissue integration on the fascial side (assessed by resistance to isolate the integrated mesh from the tissue) as compared to the control uncoated mesh.

Figure 1C:
Figure 2A:
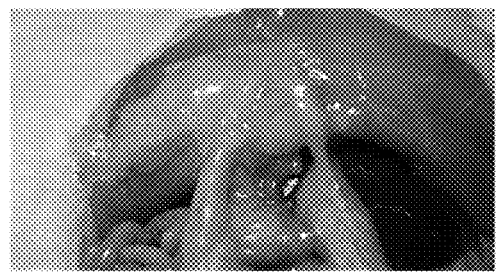
Figure 2B:
Figure 2C:

The results obtained also indicate that wet fibrin sealant pre-coated mesh fabrics were more efficient in adhesion reduction as compared to spraying the fibrin sealant onto a mesh which is placed in the surgery area during surgery (compare FIGS. 1C and 2C with 3B, 4B, 5B).

Example 3: Effect of Freeze Drying or Vacuum Drying Procedure on the Stability of the Fibrin Sealant Coated Layer In the previous example it was shown that wet pre-coated mesh fabrics are better in adhesion prevention than in situ spraying of fibrin sealant. To provide a pre-coated mesh with an extended shelf life, the pre-coated mesh can be supplied in a dry form and re-hydrated before application into the wounded tissue if desired. The following example was aimed to examine the stability of a pre-coated and dried fibrin sealant mesh. Two drying procedures were tested: freeze or vacuum drying.

For this purpose, the mesh fabrics were cut to 2.54×2.54 cm (6.45 cm$^2$) pieces, coated with an equal volume of thrombin and BAC1 (the total fibrin sealant amount used for each mesh is listed in Table 4 and 5 under wet FS). Then, the coated meshes were either freeze or vacuum dried as described above. In this experiment the meshes were not subjected to surface plasma activation prior to the coating step.

The mesh fabrics were weighed before spraying (mesh), after spraying (mesh+wet fibrin sealant; FS) and after drying procedure (data not shown).

The mesh type, the mesh weight, the mesh+wet FS weight, the wet FS weight, the dried FS weight, the water loss and the dry FS per cm$^2$ are specified in Table 4 and 5 below for freeze and vacuum drying procedures, respectively.

TABLE 4

The characteristics of fibrin coated mesh fabrics after freeze drying.

| Mesh Type | Mesh (mg) | Mesh + wet FS (mg) | * Wet FS (mg) | ** Dry FS (mg) | *** Water loss (%) | **** Dry FS/cm$^2$ (mg) |
|---|---|---|---|---|---|---|
| 403 | 33.8 | 688.5 | 654.7 | 105.5 | 83.89 | 16.35 |
| 404 | 22.9 | 684.3 | 661.4 | 104.6 | 84.19 | 16.21 |
| 601 | 57.9 | 715.4 | 657.5 | 107.1 | 83.71 | 16.60 |
| 602 | 61.5 | 470.3 | 408.8 | 61.8 | 84.88 | 9.58 |

TABLE 5

The characteristics of fibrin coated mesh fabrics after vacuum drying.

| Mesh Type | Mesh (mg) | Mesh + wet FS (mg) | * Wet FS (mg) | ** Dry FS (mg) | *** Water Loss (%) | **** Dry FS /cm$^2$ (mg) |
|---|---|---|---|---|---|---|
| 601 | 63.6 | 664.6 | 601 | 160.7 | 73.3 | 24.91 |
| 601 | 65.8 | 735.7 | 669.9 | 174.7 | 73.9 | 27.09 |
| 404 | 24.7 | 355.7 | 331 | 79.3 | 76.0 | 12.29 |
| 404 | 24.3 | 383.3 | 359 | 81.9 | 77.2 | 12.70 |
| 404 | 23.5 | 243.3 | 219.8 | 63.5 | 71.1 | 9.84 |
| 404 | 26 | 339.4 | 313.4 | 79.5 | 74.6 | 12.33 |
| 404 | 23.9 | 238.1 | 214.2 | 61.9 | 71.1 | 9.60 |
| 404 | 24.6 | 313.5 | 288.9 | 74.6 | 74.2 | 11.57 |
| 404 | 23.1 | 188.8 | 165.7 | 51.5 | 68.9 | 7.98 |
| 404 | 25.5 | 193.7 | 168.2 | 55.4 | 67.1 | 8.59 |
| 404 | 23 | 176.1 | 153.1 | 51.8 | 66.2 | 8.03 |
| 404 | 23.4 | 155.8 | 132.4 | 46 | 65.3 | 7.13 |
| 404 | 23.6 | 204.6 | 181 | 55.6 | 69.3 | 8.62 |
| 404 | 25.3 | 384.3 | 359 | 88.1 | 75.5 | 13.66 |

* The weight of the wet FS was calculated by subtracting the weight of the mesh (column 2) from the weight of the mesh + wet FS (column 3).
** The weight of the dry FS was calculated by subtracting the weight of the mesh (column 2) from the weight of the dried mesh (data not presented).
*** Water loss was calculated as follows: [(wet FS weight − dry FS weight)/wet FS weight] × 100.
**** The fibrin sealant per cm$^2$ was calculated as dry FS (column 5)/6.45 cm$^2$.

The water activity (measured by AquaLab Water Activity Meter: Series 3TE; Decagon Devices according to the manufacturer's instructions) of these fibrin coated mesh fabrics was higher than 0.6.

A visual stability assessment of the dried pre-coated mesh revealed that the fibrin coating was unstable in both drying procedures, i.e. freeze and vacuum drying, since the coating was discontinuous and underwent flaking.

Example 4: The Effect of Cross-Linking of the Fibrin Layer on the Stability of the Coating The previous example showed that freeze or vacuum drying of the fibrin sealant pre-coated mesh resulted in an unstable coating structure.

The following example illustrates the effect of cross-linking of the fibrin coating on the stability of the coating.

PPKM403 mesh fabric was cut to 2.54×2.54 cm pieces, placed in a tray and sprayed with about 0.3 ml fibrin sealant (equal quantities of thrombin and BAC1 solutions). Then, the wet coated mesh fabrics were put in an oven at 37° C. for about 30 minutes until a clot was formed. The samples were hanged on a hook in order to avoid attachment of the coated mesh onto the tray. This step was followed by vacuum drying at 4 mbar for 1.5 hours and cross-linking the fibrin coating in an oven (Carbolit PF200) at 120° C. for 3 hours. Control groups were prepared in the same way except for the cross-linking procedure.

In use the dried coated mesh can be re-hydrated prior to implantation. Thus, qualitative determination of the stability of the dried-cross linked fibrin coating layer (see materials and methods) was carried out before and after dipping the cross-linked fibrin coated mesh in saline (the meshes were dipped in saline for 5 minutes). The results are presented as a stable (Y) or an un-stable (N) fibrin coating (Table 6).

TABLE 6

Stability of the cross-linked fibrin coated mesh fabrics.

| Sample | Stability | |
|---|---|---|
| | Before saline wetting | After saline wetting |
| Dried cross-linked coated mesh | Y | Y |
| Dried cross-linked coated mesh | Y | Y |
| Dried cross-linked coated mesh | Y | Y |
| Dried coated mesh | Y | N |

The results indicate that following saline re-hydration the cross-linked coated mesh exhibited increased stability of the fibrin coating layer compared with the coated mesh which was not subjected to cross-linking treatment.

These results were verified in another set of experiments. PPKM602 mesh fabric was cut to 2.54×2.54 cm pieces and coated as described above. Afterwards, the dried-mesh fabrics were subjected to gamma irradiated at a dose of 10±5 kGy. Control groups were prepared in the same manner apart from the irradiation procedure.

Qualitative stability assessment (see materials and methods) of these pre-coated meshes was carried out before and after wetting with saline as described above. The results are presented in Table 7.

TABLE 7

Stability of irradiated cross-linked fibrin coated mesh fabrics.

| Sample | Stability | |
|---|---|---|
| | Before saline wetting | After saline wetting |
| Dried cross-linked coated mesh | Y | Y |
| Dried cross-linked coated mesh | Y | Y |
| Dried cross-linked coated mesh | Y | Y |
| Dried cross-linked coated mesh | Y | Y |
| Dried cross-linked coated mesh | Y | Y |
| Dried cross-linked coated mesh | Y | Y |

The results show that cross-linking and irradiation procedures resulted in a stable dried pre-coated mesh fabric.

Example 5: The Effect of the Dried Cross-Linked Coated Mesh on the Adhesion Level The previous example showed that cross-linking stabilizes the fibrin coating on the substrate. The following experiment was carried out in order to find out whether the cross-linking procedure affects the anti-adhesive properties of the pre-coated mesh. For this purpose, the adhesion grading after implantation of the irradiated and cross-linked fibrin coated mesh (mentioned in the previous example) in the surgery area was examined. Uncoated mesh matrices were used as reference.

Figure 6A:
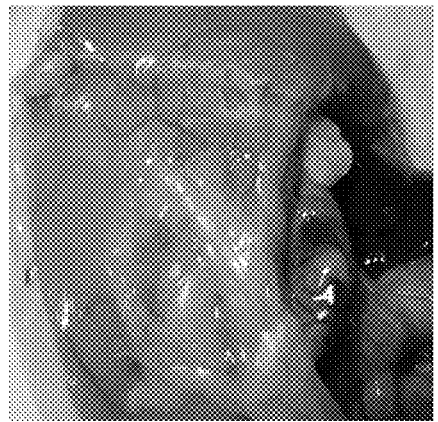
FIGS. 6-7 show the adhesion level in the operated area 17 and 30 days following the surgery procedure, respectively, in animals implanted with uncoated (control groups; A), and cross-linked coated mesh fabrics (B).
Figure 6B:
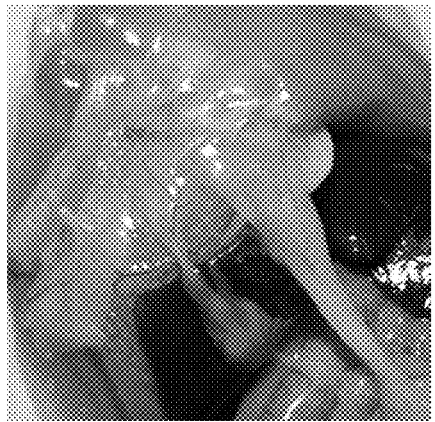
Figure 7A:
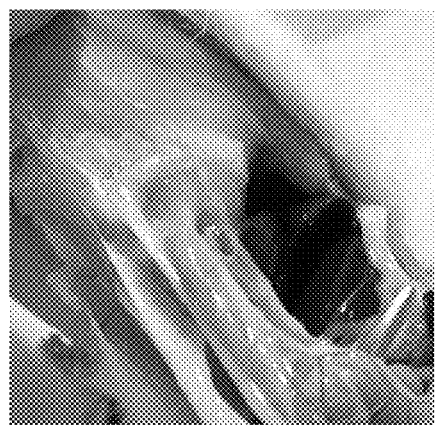
Figure 7B:

FIGS. 6 and 7 show the adhesion level in the operated area 17 and 30 days following the surgery procedure, respectively in animals implanted with an uncoated mesh (control groups; A), and irradiated and cross-linked fibrin coated mesh fabrics (B).

TABLE 8

The anti-adhesive effect of the cross-linked fibrin coated mesh.

| Animal | Sample | FS (ml) | Days in vivo | *Adhesion grading |
|---|---|---|---|---|
| 1 | Uncoated mesh | — | 17 | 3 |
| 2 | Uncoated mesh | — | 30 | 3 |
| 3 | Cross-linked coated mesh | 0.3 | 17 | 2 |
| 4 | Cross-linked coated mesh | 0.3 | 30 | 1 |

*The adhesion grading was assigned based on Smith et al. and Diamond et al. scoring methodology (see materials and methods).

The results indicated that the irradiated-cross-linked fibrin coated mesh matrices were superior to the uncoated mesh with regard to adhesion prevention.

Example 6: The Stability of a Fibrin Sealant Pre-Coated Mesh Fabric Dried at Room Temperature Example 4 shows that a cross-linked fibrin sealant pre-coated mesh exhibited increased stability of the fibrin coating layer.

The present example was aimed to examine the stability of a fibrin sealant pre-coated mesh fabric containing about 3% water, 65% salt and 32% proteins (such as fibrinogen, thrombin, Factor XIII, fibronectin etc.) which was dried at room temperature.

The mesh fabrics were coated with 45 µl BAC1 per $cm^2$, followed by coating with 4.28 µl thrombin per $cm^2$ and the meshes were left to dry at room temperature overnight. Prior to coating the meshes were subjected to plasma surface activation technology. An example of a laboratory plasma machine is Type Nano, from Diener Electronic. The process included activation of the surface with oxygen at a chamber pressure of 0.4 mbar and a power of 200 W for 300 seconds.

The dried pre-coated meshes were incubated at room temperature for 2 to 3 weeks and up to 6 months under non sterile conditions and qualitative stability assessments of the coating were carried out (see materials and methods).

It was apparent that the fibrin coating layer was stable, and the layer did not undergo flaking. No visible deterioration was evident.

These results were corroborated in another set of experiments. PPKM601 polypropylene meshes were subjected to plasma surface activation as described above, coated with 45 µl BAC1 per $cm^2$, followed by coating with 4.28 µl thrombin per $cm^2$. The coated mesh was left to dry for 15 hours at room temperature under ambient air. The meshes were placed in a sealed package which contained silica desiccant and kept at room temperature until assayed.

The water content (measured using the Karl Fischer Titration method as described above) and water activity (measured by AquaLab Water Activity Meter: Series 3TE; Decagon Devices according to the manufacturer's instructions) were measured.

The water content in these dried pre-coated mesh fabric was lower than 10% and the water activity was lower than 0.6.

Advantageously, an implantable device having a dried coating of stabilized fibrin with reduced water activity reduces susceptibility to microbial contamination; thus it can be stored for extended period of time and is superior for medical applications.

Example 7: The Effect of Mesh Fabrics Coated with Dried Fibrin which Contains a High Concentration of Salt on Postoperative Complications The previous example shows that mesh fabrics coated with dried fibrin which contains a high concentration of salt are stable under non sterile conditions. The present example assesses the effect of these stabilized pre-coated meshes on postoperative tissue adhesion formation and on adherence of bacteria to the mesh in an in vivo setting. Inclusion of high salt concentration in the fibrin was carried out to increase stabilization. The inclusion of salt into the coating was carried out prior to clot formation by using BAC (as specified above) which comprises 100 mg/ml tranexamic acid at pH 7.

PPKM601 polypropylene meshes were subjected to plasma surface activation as described above (Example 6) and coated 45 μl BAC1 per cm$^2$, followed by coating with 4.28 μl thrombin per cm$^2$. The coated mesh was left to dry for 15 hours at room temperature under ambient air. Afterwards, the coated mesh was placed in a sealed package which contains silica desiccant and kept at room temperature until use. An abdominal wall defect model was used in this experiment. Before implantation of the mesh fabrics into the surgery area, the meshes were dipped in 70% ethanol and rinsed with sterile PBS in a test-tube for 5 minutes. When applying the mesh into the rat, the uncoated side faced the defect. Uncoated mesh fabrics were used as control. The adhesion level was evaluated using 12 animals, of which, 6 were implanted with the stabilized fibrin-coated mesh (i.e. mesh coated with dried fibrin which contains a high concentration of salt) and 6 with the uncoated mesh. A 1.7×3.2 cm mesh was implanted. The animals were sacrificed four weeks after study initiation and the meshes were photographed. The degree of adhesion formation in the surgery area was evaluated in each animal. The evaluation parameters included the percent coverage of mesh surface by adhesions (0-100% coverage) and the strength of tissue adhesion between the mesh and the omentum, liver and intestine (graded from 0-3 based on Toosie et al. 2000).

Figure 8:
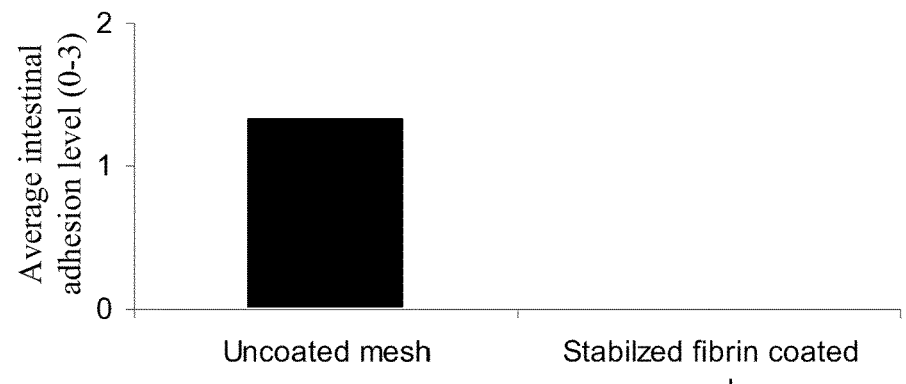
FIG. 8 shows the average strength of intestinal adhesions to the surface of the mesh (average adhesion level) in the animals implanted with the uncoated and the stabilized fibrin coated mesh.

Table 9 shows the strength evaluation of tissue adhesion to the mesh surface. The adhesion score of the different visceral organs was summed up in each animal (listed in Table 9 under Total) and the average value was calculated for each group (stabilized fibrin coated mesh and uncoated mesh). FIG. 8 shows the average strength of intestinal adhesions to the surface of the mesh (average adhesion level) in the animals implanted with the uncoated and the stabilized fibrin coated mesh. The results are extracted from Table 9 (see the score for intestinal adhesions presented in Table 9).

TABLE 9

Strength of intra-peritoneal adhesions to the mesh surface by tissues of different visceral organs.

|  | Animal | Omentum | Liver | Intestine | Total | Average |
|---|---|---|---|---|---|---|
| Stabilized Fibrin Coated Mesh | 1 | 2 | 3 | 0 | 5 | 4.5 |
|  | 2 | 1 | 3 | 0 | 4 |  |
|  | 3 | 3 | 0 | 0 | 3 |  |
|  | 4 | 1 | 3 | 0 | 4 |  |
|  | 5 | 2 | 3 (2 lobes) | 0 | 5 |  |
|  | 6 | 3 | 3 | 0 | 6 |  |
| Uncoated Mesh | 7 | 3 | 3 | 0 | 6 | 6.3 |
|  | 8 | 2 | 0 | 2 | 4 |  |
|  | 9 | 3 | 3 (2 lobes) | 0 | 6 |  |
|  | 10 | 3 | 3 | 3 | 9 |  |
|  | 11 | 1 | 3 | 0 | 4 |  |
|  | 12 | 3 | 3 | 3 | 9 |  |

* The adhesion grading was assigned based on Toosie et al. 2000 (see materials and methods).

As seen in Table 9 the average strength of attachments to the stabilized fibrin coated mesh was 4.5 versus 6.3 average strength of attachments to the uncoated mesh.

Also, there were no apparent adhesions involved with the intestine in the animals implanted with the stabilized fibrin coated mesh. In comparison, intestinal adhesions were found in the animals treated with the uncoated meshes (see the score for intestinal adhesions in Table 9 and FIG. 8).

Importantly, it can be seen that the stabilized fibrin coated mesh had a similar efficacy in adhesion reduction as the pre-coated and wet fibrin sealant mesh when relating to adhesions involved with the intestine [no adhesions were observed in both meshes; see the adhesion score of intestinal adhesions in animals treated with the stabilized fibrin coated mesh in Table 9 and the adhesion score in animals treated with the pre-coated and wet fibrin sealant mesh in Table 3, 30 days following implantation of the mesh)].

The percentage of mesh area covered by adhesions in the different meshes is summarized in Table 10.

TABLE 10

The percentage of the mesh surface covered by adhesions.

|  | Animal | Coverage (%) | Average (%) |
|---|---|---|---|
| Stabilized fibrin-coated mesh | 1 | 30 | 24.1 |
|  | 2 | 10 |  |
|  | 3 | 15 |  |
|  | 4 | 10 |  |
|  | 5 | 40 |  |
|  | 6 | 40 |  |
| Uncoated mesh | 7 | 40 | 46.2 |
|  | 8 | 20 |  |
|  | 9 | 60 |  |
|  | 10 | 75 |  |
|  | 11 | 10 |  |
|  | 12 | 72 |  |

The average of the mesh covered by adhesions was 24.1% in the stabilized fibrin-coated mesh compared with 46.2% in the uncoated mesh (Table 10).

The pathogenic load of the stabilized fibrin-coated mesh and the uncoated mesh was assessed in an abdominal wall defect model as specified above (see Bacterial Colonization of the Mesh and the Underlying Tissue in the materials and methods section). After suturing the mesh (1.7×2.7 cm) over the created defect, the mesh was held horizontally and 0.1 ml PBS with or without 5×10$^7$ CFU *Staphylococcus aureus*

(ATCC 29213) was applied to the surface of the mesh. The mesh was held in the horizontal position for 5 minutes. In total 12 animals were used, 8 animals were subjected to bacterial spiking (4 animals were implanted with the stabilized fibrin coated mesh and 4 animals were implanted with the uncoated mesh) and 4 animals without bacterial spiking (2 animals were implanted with the stabilized fibrin coated mesh and 2 animals were implanted with the uncoated mesh). The animals were sacrificed 5 days after the implantation of the mesh.

Figure 9:
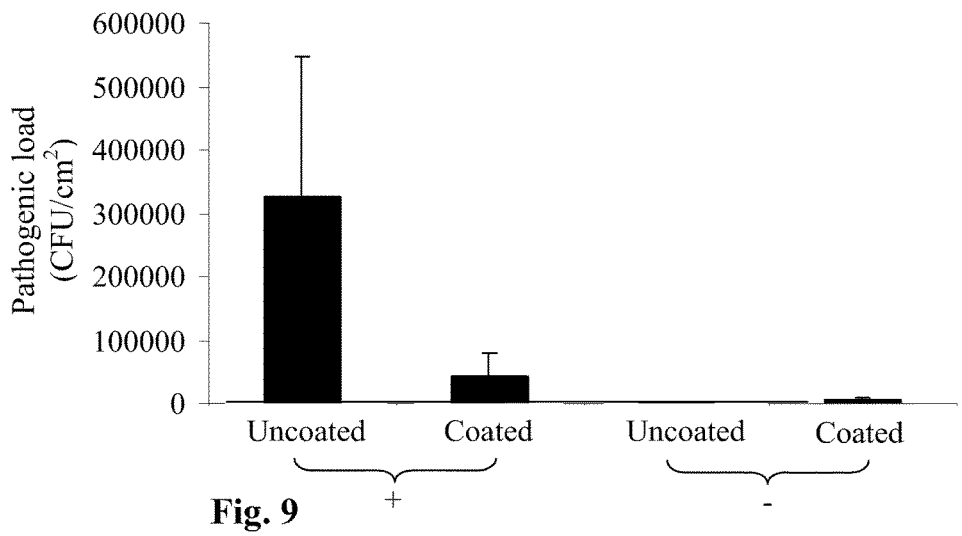
FIG. 9 shows the colony-forming units (CFU) per $cm^2$ of mesh surface in dried-fibrin coated meshes and uncoated meshes with (+) or without (−) bacterial spiking 5 days following repair of abdominal wall defects in a rat model.

FIG. 9 shows the colony-forming units (CFU) per $cm^2$ of mesh surface 5 days following the repair of the abdominal wall defect. The meshes were evaluated with (+) or without (−) bacterial spiking.

The results show that in the group subjected to bacterial contamination stabilized fibrin-coated mesh resulted in a significantly lower bacterial count compared to the uncoated mesh (p<0.05).

These results show the advantage of using an implantable surgical device comprising a coating of stabilized fibrin, since using this device results in reduction of surgically related complications such as intestinal adhesions and/or infections.

Example 8: The Effect of the Stabilized Fibrin-Coated Mesh on the Adhesion Level in Intra-Abdominal Contaminated Model The abdominal cavity has a potential risk for bacterial contamination. Studies (Brown et al. "Comparison of prosthetic materials for abdominal wall reconstruction in the presence of contamination and infection". Ann Surg. 1985; 201:705-711) indicate that the presence of bacterial contamination during abdominal wall defect reconstitution may result in serious clinical complications such as increased adhesion level.

The previous example showed that in the group subjected to bacterial contamination the stabilized fibrin coated mesh resulted in a lower bacterial count compared to the uncoated mesh. The following example examines the efficiency of the stabilized fibrin-coated mesh in minimizing visceral adhesions and reducing the infection level in the operated area in the setting of bacterial contamination.

Fibrin-Coated Mesh Preparation.

Prolene Soft Mesh (SPM; manufactured by Ethicon) was subjected to plasma surface activation as described above (Example 6) and coated with 90 μl per $cm^2$ BAC1 and 10 μl per $cm^2$ thrombin (BAC1 and thrombin as listed above). The coated mesh was left to dry at room temperature in ambient air overnight. The dried mesh was cut into 1.7×2.7 cm pieces, sealed in an aluminum pouch and kept at 2-8° C. until use. SPM mesh laminated with an oxidized regenerated cellulose (ORC) fabric, which is widely used to reduce the extent and severity of tissue attachment to the mesh, was used as reference (the SPM was encapsulated by using a polydioxanone polymer). The ORC-coated mesh was pre-sterilized by gamma irradiation and cut to 1.7×2.7 cm size under sterile conditions. Both meshes were coated on one side only.

The abdominal wall defect model was used as specified above. Before implantation of the stabilized fibrin-coated mesh, the mesh was sterilized by dipping in 70% ethanol and re-hydrated by soaking in saline for 5 minutes. The two mesh types were applied onto the defect with the uncoated side facing the defect. Following suturing of the mesh onto the created defect, the mesh was held horizontally while 0.1 ml PBS with (n=8) or without (n=4) $5×10^8$ CFU *Staphylococcus aureus* (ATCC 29213) was applied onto the surface of the mesh. The meshes were held in horizontal position for 5 minutes. Evaluation of the adhesion and infection level was carried out 5 days following the surgery procedure. Several adhesion parameters were assessed: 1) the strength of intra-abdominal attachment to the surface of the mesh (tenacity of the adhesion); 2) the percent of mesh area covered with adhesions; and 3) the incidence of intestinal adhesions.

The results show that the average strength of intra-abdominal tissue attachment to the mesh surface and the percentage of mesh area covered by adhesions were similar in both tested meshes in the non-contaminated group (see Table 11 and 12, respectively). However, in the contaminated group it can be seen that the strength of tissue attachment to the fibrin-coated mesh was lower as compared to the strength attachment level to the ORC-coated mesh (Table 11). In addition, the percentage of mesh covered by adhesions in the contaminated group was significantly lower in the fibrin coated mesh as compared to the ORC-coated mesh (63.13±34.63 vs. 93.13±12.80 for the fibrin-coated mesh and the ORC-coated mesh, respectively; p=0.037).

These results show the superior performance of the fibrin coated mesh in contaminated area.

Formation of intestinal adhesions. Intestinal adhesions may lead to the most severe complications during abdominal wall defect repair (Ellis et al. "The causes and prevention of intestinal adhesions". Br J. Surg. 1982; 69:241-243; and Ellis et al. "The clinical significance of adhesions: focus on intestinal obstruction". Eur J Surg Suppl. 1997; 5-9). Therefore, formation of intestinal adhesions was monitored 5 days following the implantation of the coated meshes. No intestinal adhesions were observed in both tested meshes in the non-contaminated group.

Under bacterial contamination, the number of animals with intestinal adhesions was lower in the group implanted with fibrin-coated meshes as compared to animals implanted with ORC-coated mesh (Table 13).

In addition, the formation of infection in the operating area was assessed by monitoring the number of animals which developed intra-abdominal abscesses.

The results indicate that both meshes prevented abscess formation in the non-contaminated group. Importantly, none of the animals implanted with fibrin-coated mesh were found to have abscesses or any other signs of infection in the contaminated model. In comparison, all animals implanted with ORC-coated mesh in contaminated setting developed abscesses 5 days following the implantation.

The above results show that the stabilized fibrin coated mesh of the invention is efficient in reducing the adhesion level and/or in preventing formation of infection in contaminated fields and thus can be effectively used in areas which have potential risk for developing bacterial contamination.

TABLE 11

The effect of stabilized fibrin-coated mesh on the tenacity of the adhesion.

| | Sample | *Adhesion grading (Average) |
|---|---|---|
| Non-contaminated group | Fibrin-coated mesh | 0.165 |
| | ORC-coated mesh | 0.5 |
| Contaminated group | Fibrin-coated mesh | 1.04 |
| | ORC-coated mesh | **Higher than the adhesion grading in the fibrin-coated mesh group with bacteria contamination. |

*The adhesion grading was assigned as indicated in Toosie et al. 2000 (see materials and methods).
**This parameter was difficult to assess due to the structure of the adhesion mass formed and the presence of abscesses.

TABLE 12

The effect of stabilized fibrin-coated mesh
on the percentage of mesh covered by adhesions.

| | Sample | Mesh coverage by adhesions (%) |
|---|---|---|
| Non-contaminated group | Fibrin-coated mesh | 15.00 ± 19.15 |
| | ORC-coated mesh | 0.00 |
| Contaminated group | Fibrin-coated mesh | *63.13 ± 34.63 |
| | ORC-coated mesh | 93.13 ± 12.80 |

*p = 0.037 as compared to ORC-coated meshes with bacterial contamination.

TABLE 13

The effect of stabilized fibrin-coated mesh
on the incidence of intestinal adhesions.

| | Sample | The number of animals with intestinal adhesions |
|---|---|---|
| Non-contaminated group | Fibrin-coated mesh | 0/4 |
| | ORC-coated mesh | 0/4 |
| Contaminated group | Fibrin-coated mesh | 3/8 |
| | ORC-coated mesh | 6/8 |

TABLE 14

The effect of stabilized fibrin-coated mesh on abscesses formation.

| | Treatment | The numbers of animals with abscess |
|---|---|---|
| Non-contaminated group | Fibrin-coated mesh | 0/4 |
| | ORC-coated mesh | 0/4 |
| Contaminated group | Fibrin-coated mesh | 0/8 |
| | ORC-coated mesh | 8/8 |

Example 9: The Effect of Fibrin-Coated Mesh on Bacterial Colonization and Infection Level of the Mesh and the Surrounding Tissue The present example was aimed to examine the ability of the stabilized fibrin-coated mesh to minimize bacterial colonization and reduce the infection level of the mesh and the surrounding tissue. The subcutaneous model in mice was used as described above. The efficacy of the stabilized fibrin coated mesh was compared to SURGISIS®, a commercial mesh which is intended for hernia reconstruction. For this purpose, 1-cm diameter light polypropylene meshes were subjected to plasma surface activation as described above (Example 6) and coated with 90 µl per cm² BAC1 and 10 µl per cm² thrombin (BAC1 and thrombin as listed above). The coated meshes were left to dry at room temperature in ambient air overnight, sealed in an aluminum pouch and kept at 2-8° C. until use. The fibrin coated mesh was sterilized using gamma irradiation at a dose of 12±2 kGy and re-hydrated in saline prior to the implantation procedure. SURGISIS® was supplied in a sterile package and applied into the subcutaneous pocket according to the manufacturer's instructions. The following parameters were evaluated (as listed above in the materials and section method under Subcutaneous model in Mice): 1) the bacterial count on the implanted mesh and the surrounding tissue; and 2) the inflammatory reaction level.

Figure 10:
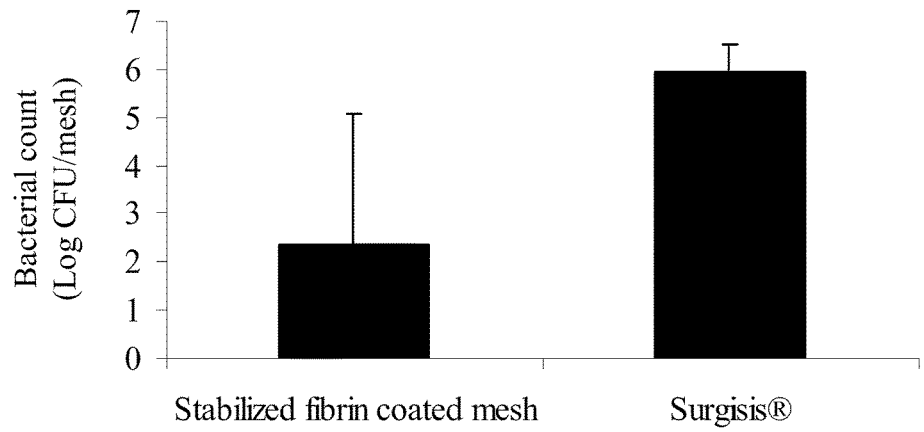
FIG. 10 shows the average CFU per mesh 15 days following implantation of the mesh in a subcutaneous model. The efficacy of the dried fibrin-coated mesh in reducing bacterial colonization of the mesh and the surrounding tissue was compared to SURGISIS® mesh, a commercially available mesh intended for hernia reconstruction.

FIG. 10 shows the average CFU per mesh 15 days following implantation of the mesh in a subcutaneous model. The results show that the stabilized fibrin coated mesh resulted in a significant reduction in bacterial count as compared to SURGISIS® mesh.

Figure 11:
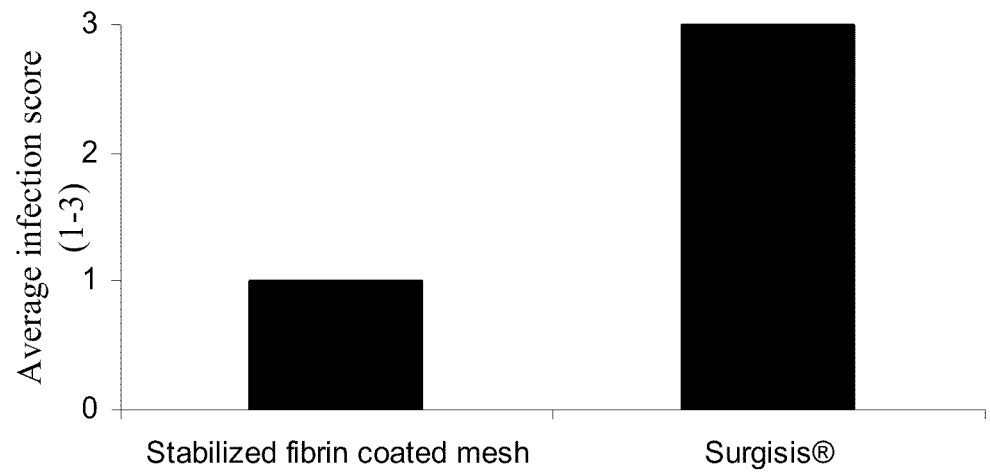
FIG. 11 shows the average infection score graded from 1 to 3 of the meshes described in FIG. 10. While the grade 1 describes no infection, explant flat, tissue looks healthy; the grade 2 describes some infection, explant swollen, slightly necrotic; and the grade 3 describes sever infection, explants encapsulated and tissue necrotic.

FIG. 11 shows the infection score of the different explants 15 days following the operation. It is apparent that the fibrin coated mesh resulted in a lower infection score as compared to SURGISIS® mesh (level 1 and level 3, respectively). Of note, no variation in the infection score of the explants was found within each group.

Example 10: The Water Content and the Water Activity of the Dried Fibrin Coating Composition An implantable device having a water activity of equal to or less than 0.6 following the drying procedure may result in a longer shelf-life and improved functional characteristics of the product. The water content changes as the water activity is increased or decreased. Thus, the following example was carried out to map the relationship between the water content and the water activity of the product and to asses what is the water content in a fixed water activity.

For this purpose, a moisture sorption isotherm was formed using the AquaSorp Isotherm Generator (Decagon Devices). The AquaSorp produces adsorption and desorption isotherm curves using the Dynamic Dewpoint Isotherm method (DDI). In principle, desorption curve is formed by drying the sample and determining the water content in the sample and adsorption curve is formed by wetting the sample and determining the water content in the sample. Drying and wetting of the sample is achieved by decreasing (drying) or increasing (wetting) the relative humidity (RH %=100×$a_w$) in the chamber. The isotherms were formed in the following parameters: a temperature of 25° C., a flow rate of 100 ml/min, and a water activity in the range of from about 0.08 to about 0.9.

Isotherms were formed for two types of fibrin coated meshes as specified below. Prior to the coating step the polypropylene mesh was subjected to plasma surface activation technology as described above.

Sample 1 Preparation.

The plasma-activated mesh (1.7×2.5 cm) was coated with 92 µl BAC1 per cm², followed by coating with 9.2 µl thrombin per cm² (the BAC1 and thrombin used are as listed above). The coated mesh was left to dry overnight at ambient room temperature and humidity of ~50%. The mesh was sealed in an aluminum package and incubated in the refrigerator (4° C.) until assayed.

Sample 2 Preparation.

Following plasma activation treatment, the mesh (2×4.5 cm) was coated with BAC2 and thrombin components. The BAC2 component was diluted with purified water (1:6) to decrease the liquid viscosity and the mesh was coated with 136.73 µl of the diluted BAC2 per cm². Then, the mesh was coated with 8.78 µl thrombin per cm². The coated mesh was dried for 18 hours at 25° C. and humidity of 60%, packed in a sterile aluminum packaging and incubated in the refrigerator (4° C.) until assayed.

Both meshes were coated using the BioSpot coating process (BioFluidix, Germany) BAC1 composition comprises a higher salt content than BAC2 composition (see composition formulation above).

Figure 12:
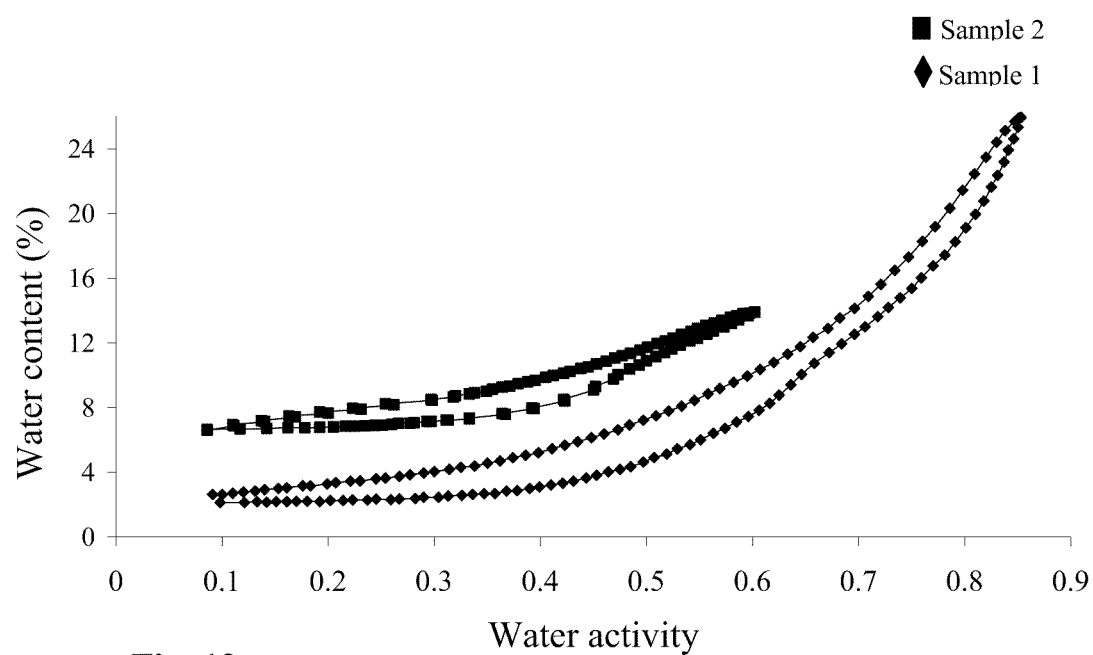
FIG. 12 shows desorption (upper curve of each sample) and adsorption (lower curve of each sample) isotherm curves for two different meshes coated with stabilized fibrin.

Desorption (upper curve of each sample) and adsorption (lower curve of each sample) curves for both samples are shown in FIG. 12. The production process includes drying of the coated device thus evolution of the sample water content was determined according to the desorption curve. It can be seen that a higher concentration of a solute results in a lower water content in a fixed water activity. For example, sample 1 which contained a higher salt concentration (about 60%) had a water content of 10% in a water activity of 0.6 whereas sample 2 (which has 23% salt content) had a water content of 14% in the same water activity.

Example 11: The Effect of the Solute Concentration on the Water Content of Dried Fibrin The following example was aimed to determine the effect of solute concentration on the water content of the dried fibrin clots. Three different solutes were used: tranexamic acid, NaCl and glycine.

Each solute was added to 5 ml BAC2 composition in a final concentration of 10% w/w. In the next step, a thrombin component (the same as listed in the materials) was diluted in water to obtain a final concentration of 100 IU/ml. Then, a fibrin clot was formed on a Teflon surface from equal quantities of the two diluted components (a total volume of 0.5 ml was used). A clot was also formed as listed above except for the addition of solute to the BAC2 composition. The Teflon surface with the different samples was transferred into a humidity chamber set to 60% RH and to a temperature of 25° C. overnight.

The water content of the dried fibrin clots were measured using the Karl Fischer Titration method as described above. The results are presented in Table 15 below.

TABLE 15

The effect of solute addition on the water content of dried fibrin clots.

| Sample | Water content (%) | Average water content (%) | *Reduction in water content (%) |
|---|---|---|---|
| BAC2 | 17.30 | 18.7 | — |
|  | 20.03 |  |  |
| Tranexamic Acid | 14.51 | 15.5 | 17% |
|  | 16.43 |  |  |
| NaCl | 14.49 | 14.4 | 23% |
|  | 14.24 |  |  |
| Glycine | 12.9 | 13.4 | 28% |
|  | 13.81 |  |  |

*The reduction in water content was calculated compared to the fibrin clots prepared with pure BAC2 composition.

The results obtained showed that addition of solute resulted in a decrease in the water content of the dried fibrin clot as compared to clots prepared from pure BAC2 composition.

What is claimed is:

1. A method for producing an improved implantable mesh for repairing an opening or a defect in a soft tissue, the mesh having a visceral and a non-visceral surface, and the visceral surface is the portion of the surface which faces away from the fascia defect and allows reduction of postoperative adhesions, the method comprising the steps of: applying at room temperature to a visceral surface of a mesh a defined volume of an aqueous solution comprising fibrinogen and an aqueous solution comprising a proteolytic enzyme that reacts with fibrinogen to convert the fibrinogen into a homogeneously distributed fibrin coating on the visceral surface, adding a solute capable of binding free water and having a molecular weight of about 1,000 Dalton or less; and drying the fibrin coating, thereby obtaining a ready to use implantable mesh comprising a stabilized dry and homogenous fibrin coating on the visceral surface for placing the non-visceral surface of the mesh facing the opening or defect and for placing the visceral surface facing away from the opening or defect for reducing postoperative adhesions.

2. The method according to claim 1, wherein the surface of the substrate is activated prior to forming the fibrin coating such as by plasma treatment.

3. The method according to claim 1, wherein said proteolytic enzyme is thrombin.

4. The method according to claim 1, wherein said opening or defect is a hernia.

5. The method according to claim 1, wherein a solute is added prior to the drying step, and wherein the concentration of said solute in the fibrin coating following the drying step is in the range of about 5%-68%, in the range of about 20%-68%, in the range of about 20%-32%, or in the range of about 51%-68%.

6. The method according to claim 1, wherein said drying is carried out by non-intensive drying.

7. The method according to claim 1, wherein the temperature during the drying step is less than 37° C.

8. The method according to claim 1, wherein after the drying step said fibrin coating comprises a residual water content of about 3% to about 20%.

9. The method according to claim 6, wherein the non-intensive drying is by air drying.

* * * * *